US009882748B2

(12) United States Patent
Ran

(10) Patent No.: US 9,882,748 B2
(45) Date of Patent: Jan. 30, 2018

(54) TECHNOLOGIES FOR CONFIGURING TRANSMITTER EQUALIZATION IN A COMMUNICATION SYSTEM

(71) Applicant: Intel Corporation, Santa Clara, CA (US)

(72) Inventor: Adee O. Ran, Maayan Baruch (IL)

(73) Assignee: Intel Corporation, Santa Clara, CA (US)

(*) Notice: Subject to any disclaimer, the term of this patent is extended or adjusted under 35 U.S.C. 154(b) by 119 days.

(21) Appl. No.: 14/580,823

(22) Filed: Dec. 23, 2014

(65) Prior Publication Data
US 2015/0256365 A1 Sep. 10, 2015

Related U.S. Application Data

(60) Provisional application No. 61/950,436, filed on Mar. 10, 2014.

(51) Int. Cl.
*H01L 25/03* (2006.01)
*H04L 25/03* (2006.01)
*B01D 3/00* (2006.01)
*C07C 51/265* (2006.01)
*C07C 63/26* (2006.01)
*C08G 63/183* (2006.01)

(52) U.S. Cl.
CPC ........ *H04L 25/03885* (2013.01); *B01D 3/009* (2013.01); *C07C 51/265* (2013.01); *C07C 63/26* (2013.01); *C08G 63/183* (2013.01)

(58) Field of Classification Search
CPC ......... H04L 25/03885; H04L 25/03878; H04L 25/03076; H04L 25/03006; H04L 7/0091; H04L 2025/03433; H04L 2025/03808; H04L 27/01
See application file for complete search history.

(56) References Cited

U.S. PATENT DOCUMENTS

2013/0301696 A1* 11/2013 Smith ................ H04L 1/24
375/229

FOREIGN PATENT DOCUMENTS

CN 103109507 5/2013

OTHER PUBLICATIONS

Chinese Office Action for Chinese Patent Application No. 201510068339.X, dated Jun. 29, 2017 (27 pages, including English translation).

* cited by examiner

*Primary Examiner* — Curtis Odom
(74) *Attorney, Agent, or Firm* — Barnes & Thornburg LLP

(57) ABSTRACT

Technologies for transmitter equalization in a communication system include reading local transmitter equalization settings from a transmitter equalization register of a first communication device and writing the local transmitter equalization settings to a transmitter equalization register of a second communication device communicatively coupled with the first communication device via a chip-to-chip communication link. Additionally, requested transmitter equalization settings may be read from the transmitter equalization register of the second communication device and written to the transmitter equalization register of the first communication device. The reading and writing process may be repeated for the opposite communication direction and for other communication lane interfaces of the first and second communication devices.

30 Claims, 14 Drawing Sheets

| PRE-CURSOR TAP VALUE | C(-1) COEFFICIENT WEIGHT |
|---|---|
| 0 | 0 ± 0.04 |
| 1 | -0.05 ± 0.04 |
| 2 | -0.1 ± 0.04 |
| 3 | -0.15 ± 0.04 |

| POST-CURSOR TAP VALUE | C(1) COEFFICIENT WEIGHT |
|---|---|
| 0 | 0 ± 0.04 |
| 1 | -0.05 ± 0.04 |
| 2 | -0.1 ± 0.04 |
| 3 | -0.15 ± 0.04 |
| 4 | -0.2 ± 0.04 |
| 5 | -0.25 ± 0.04 |

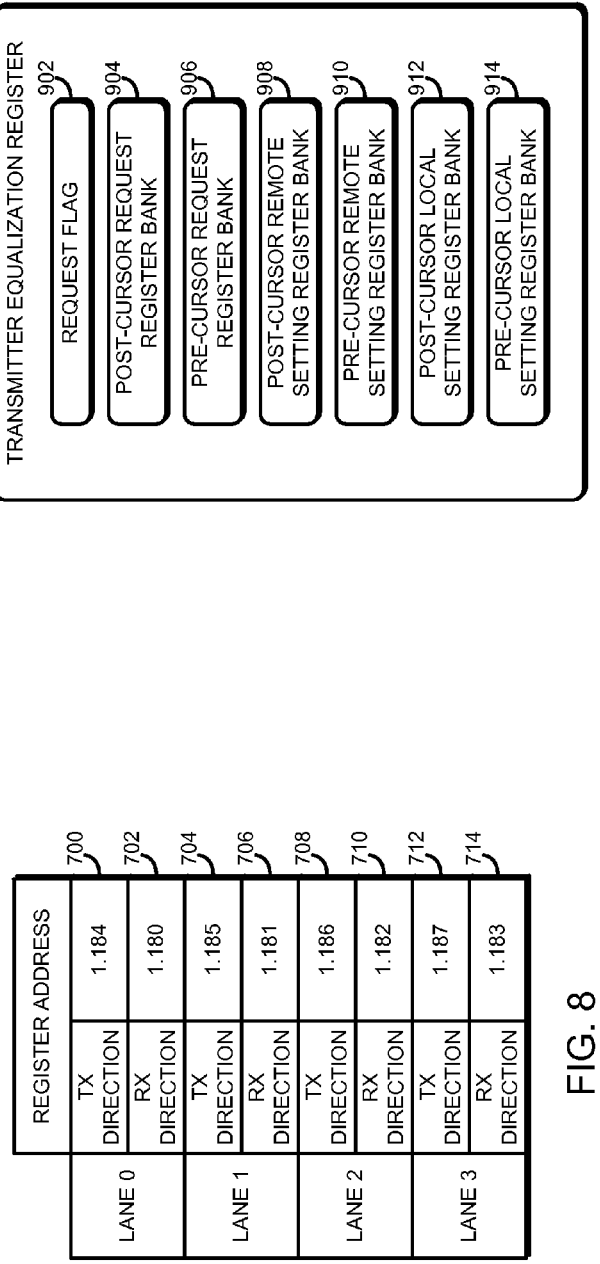
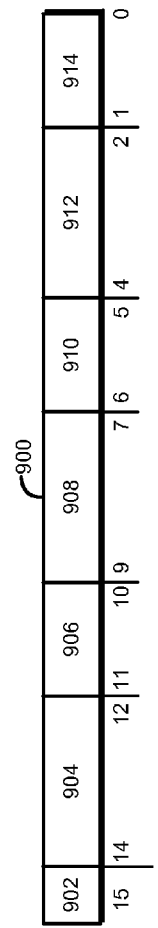
FIG. 9
FIG. 10
FIG. 8

1100

| REGISTER BANK | BIT RANGE | DESCRIPTION | | | |
|---|---|---|---|---|---|
| POST-CURSOR LOCAL SETTING 912 | 4:2 | 14 | 13 | 12 | POST-CURSOR TAP VALUE |
| | | 1 | 1 | 1 | RESERVED |
| | | 1 | 1 | 0 | RESERVED |
| | | 1 | 0 | 1 | Local_eq_c1 = 5 |
| | | 1 | 0 | 0 | Local_eq_c1 = 4 |
| | | 0 | 1 | 1 | Local_eq_c1 = 3 |
| | | 0 | 1 | 0 | Local_eq_c1 = 2 |
| | | 0 | 0 | 1 | Local_eq_c1 = 1 |
| | | 0 | 0 | 0 | Local_eq_c1 = 0 |
| PRE-CURSOR LOCAL SETTING 914 | 1:0 | 11 | 10 | | PRE-CURSOR TAP VALUE |
| | | 1 | 1 | | Local_eq_cm1 = 3 |
| | | 1 | 0 | | Local_eq_cm1 = 2 |
| | | 0 | 1 | | Local_eq_cm1 = 1 |
| | | 0 | 0 | | Local_eq_cm1 = 0 |

FIG. 12

TECHNOLOGIES FOR CONFIGURING TRANSMITTER EQUALIZATION IN A COMMUNICATION SYSTEM

CROSS-REFERENCE TO RELATED APPLICATION

The present application claims priority under 35 U.S.C. § 119(e) to U.S. Provisional Patent Application Ser. No. 61/950,436, entitled "TECHNOLOGIES FOR CONFIGURING TRANSMITTER EQUALIZATION IN A COMMUNICATION SYSTEM," which was filed on Mar. 10, 2014.

BACKGROUND

Some communication systems, such as a multi-link "top-of-rack" Ethernet switch, include a main communication controller, sometimes referred to as a "switch chip," which is typically connected to several receptacles in which optical modules may be plugged. Depending on the particular implementation, the communication controller may be configured to communicate with any number of such modules using a suitable communication interface. One such interface is the 100 Gigabit Attachment Unit Interface-4 (CAUI-4) chip-to-module interface, which is defined by the Institute of Electric and Electronics Engineers (IEEE) P802.3bm specification. The CAUI-4 chip-to-module interface enables communication between chips and modules at a data rate of up to 100 gigabits-per-second using four lanes in parallel with 25.78 gigabaud signaling on each lane. Of course, transmitting data between chips and modules at such high baud rates requires robust signal integrity, which limits the distance between the chip and respective module to a few inches to meet the low bit error ratio (BER) required by the CAUI-4 chip-to-module interface specification.

To facilitate the placement of modules at a distance greater than the typical limited distance, the CAUI-4 defines a chip-to-chip interface that facilitates the use of retimer chips to extend the overall distance between the communication controller (e.g., the switch chip) and associated module. To increase the distance even further, multiple retimers may be used in series. The increase in overall distance is accomplished by specifying transmit-side equalization in both sides of the CAUI-5 chip-to-chip link. For example, the IEEE P802.3bm, Annex 83D, Draft 2.1, specification defines the transmitter equalization as a three-tap feed forward filter having filter coefficients selected from a few possible combinations. However, the IEEE P802.bm specification does not define any specific functionality for selecting or controlling the equalization settings. Although some communications systems allow for partner-to-partner in-band back channel communication to facilitate the tuning of the filter coefficients, such in-band, back channel back channel communications is complex and can disrupt system performance.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

FIG. 8 is an simplified table of illustrative register addresses for each lane of the chip-to-chip communication interface of FIG. 7;

FIG. 9 is a simplified block diagram of an illustrative transmitter equalization register of the chip-to-chip communication interface of FIG. 7;

FIG. 10 is a simplified block diagram of the transmitter equalization register of FIG. 9 showing illustrative bit ranges for each register bank of the transmitter equalization register;

FIGS. 11 and 12 is a simplified table of illustrative register bank settings of the transmitter equalization register of FIG. 7;

DETAILED DESCRIPTION OF THE DRAWINGS

Figure 1:
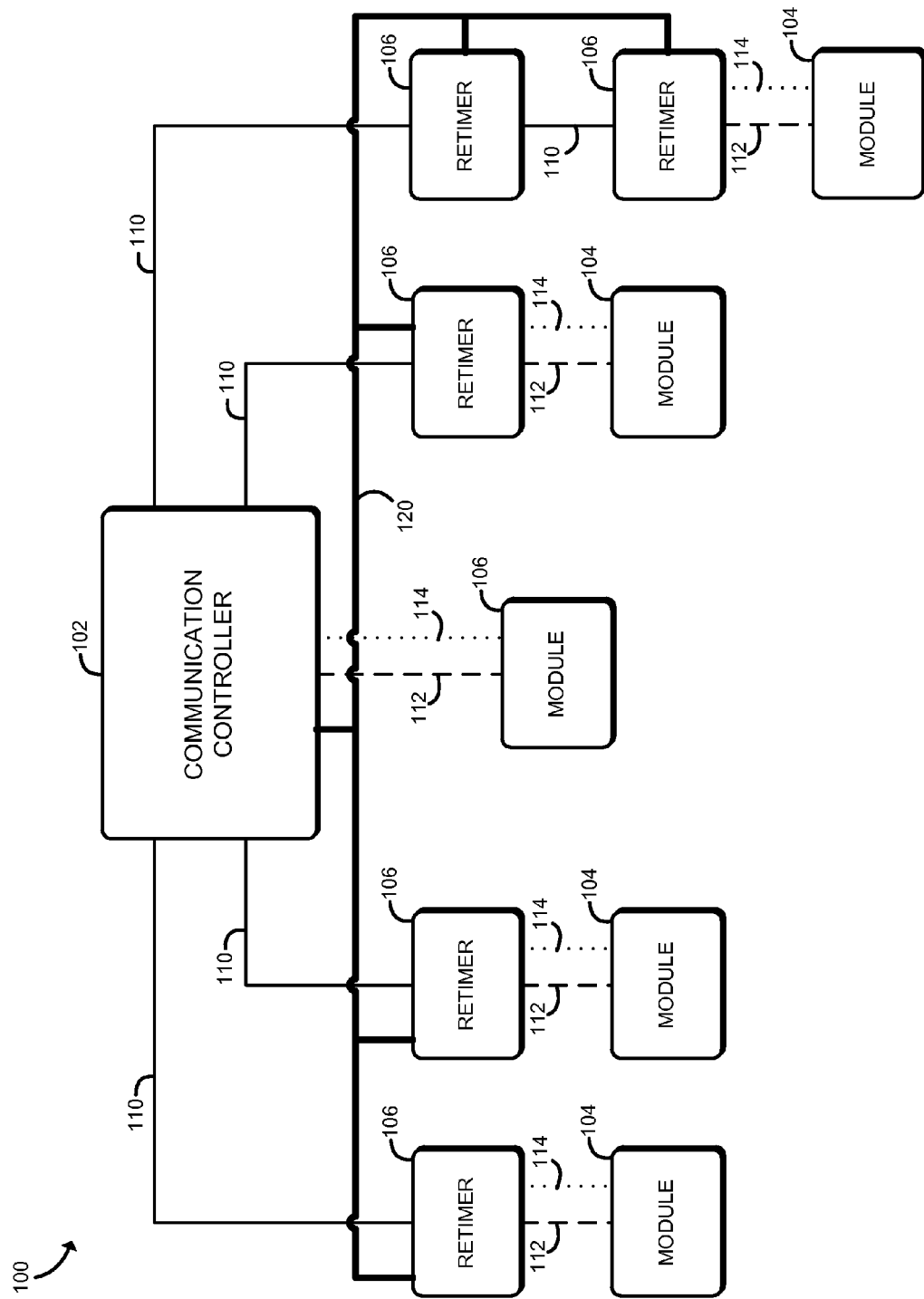
FIG. 1 is a simplified block diagram of at least one embodiment of a communication system including transmitter equalization technology.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C): (A and B); (B and C); or (A, B, and C). Similarly, items listed in the form of "at least one of A, B, or C" can mean (A); (B); (C): (A and B); (B and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative communication system 100 includes a communication controller 102, a plurality of modules 104, and a plurality of retimers 106. The communication system 100 may be embodied as, for example, an Ethernet top-of-rack switch or other communication device or system. The communication controller 102 may be embodied as a switch chip and is illustratively configured to communicate with each of the modules 104, which may be embodied as optical modules in some embodiments. In the illustrative embodiment, the communication controller 102 communicates with the modules 104 according to the CAUI-4 specification. As some of the modules 104 may be located a distance from the communication controller 102 greater than the allowed maximum distance under the CAUI-4 chip-to-module specification, the communication controller 102 may utilize one or more retimers 106 in the communication path to facilitate communications with such remote modules 104.

As shown in the illustrative embodiment of FIG. 1, the communication controller 102 is communicatively coupled to each retimer 106 via a CAUI-4 chip-to-chip communication link 110. Each retimer 106 is communicatively coupled to either an associated module 104 via a CAUI-4 chip-to-module communication link 112 and an inter-integrated circuit (I2C) communication link 114 or to another retimer 106 via CAUI-4 chip-to-chip communication link 110. For those modules 104 of the communication system 100 located within the allowable distance of the communication controller 102, the communication controller 102 is communicatively coupled directly to such local modules 104 via an associated CAUI-4 chip-to-module communication link 112. Additionally, for those modules 104 located a distance away from the communication controller 102 greater than the maximum standard distance, two or more retimers 106 may be used in series to connect the module 104 to the communication controller 102 (see, e.g., the right-most retimers 106 of FIG. 1). Each of the communication links 110, 112 illustratively includes four parallel communication lanes to facilitate communication as defined by the CAUI-4 specification.

As shown in FIG. 1, the communication controller 102 is also communicatively coupled to each retimer 106 via a dedicated communication bus 120. In the illustrative embodiment, the dedicated communication bus 120 is embodied as a management data input/output (MDIO) bus according to Clause 45 of the IEEE P802.3bm specification, but other dedicated communication buses may be used in other embodiments. As discussed in more detail below, the dedicated communication bus 120 allows the communication controller 102 to initialize, configure, and manage the transmitter filter equalization of each CAUI-4 transmitter of the communication system 100 without the requirement of communicating across the established CAUI-4 chip-to-chip communication links 110.

Figure 2:
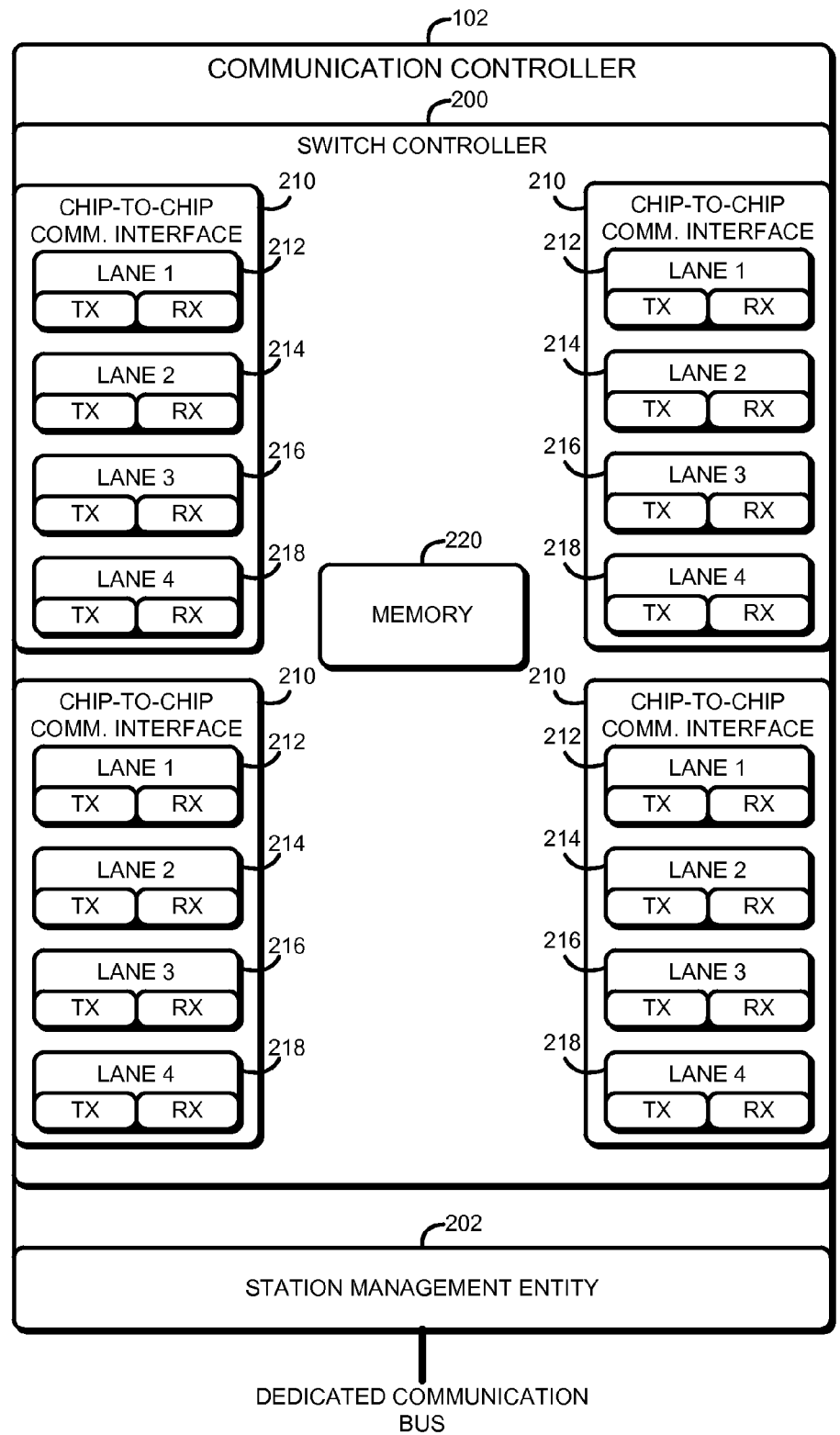
FIG. 2 is a simplified block diagram of at least one embodiment of a communication controller of the communication system of FIG. 1.

Referring now to FIG. 2, in the illustrative embodiment, the communication controller 102 includes a switch controller 200 and a station management entity 202. The switch controller 200 may be embodied as a "switch chip" and is configured to communicate with the modules 104 and/or retimers 106 according to the CAUI-4 specification. To facilitate communications with the retimers 106, the switch controller 200 may include one or more chip-to-chip communication interfaces 210. Each chip-to-chip communication interface 210 includes four communication lane interfaces 212, 214, 216, 218 with each communication lane interface 212, 214, 216, 218 including corresponding transmitter and receiver circuitry. Although only four chip-to-chip communication interfaces 210 are shown in FIG. 2, it should be appreciated that the switch controller 200 may include additional or fewer chip-to-chip communication interfaces 210 in other embodiments. Additionally, the switch controller 200 may include one or more chip-to-module communication interfaces (not shown) for facilitating communications directly with a local module 104.

The switch controller 200 also includes a memory 220. The memory 220 is illustratively embodied as a non-volatile memory. Although the memory 220 is illustratively shown as included in the switch controller 200, it should be appreciated the memory 220 may be located external to the switch controller 200 and/or to the communication controller 102. As discussed in more detail below, the memory 220 stores initial transmitter equalization settings for initializing the transmitter equalization registers of transmitters of the various chip-to-chip communication interfaces 210 of the system 100.

Figures 3, 4, 5:
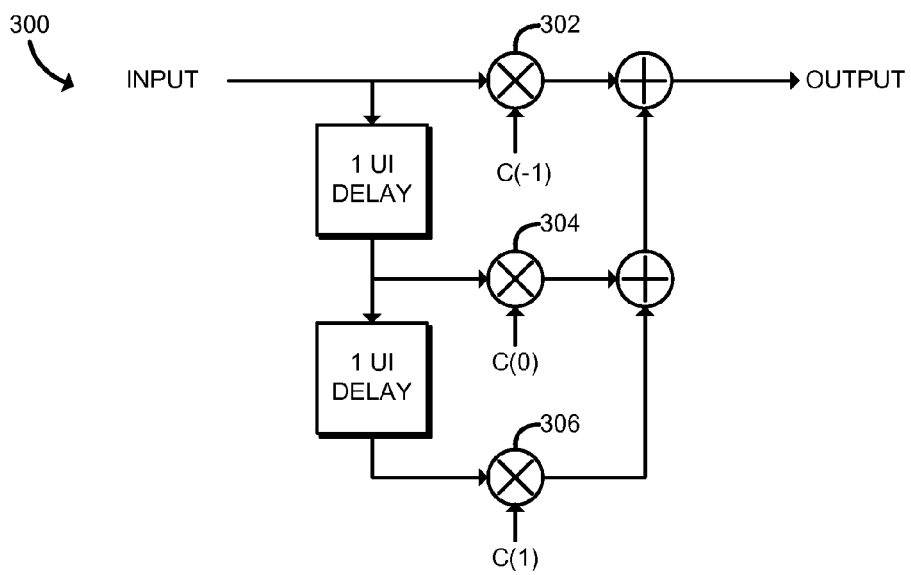
FIG. 3 is a simplified block diagram of at least one embodiment of functional model of a transmitter equalizer.
FIG. 4 is an simplified table of illustrative pre-cursor tap values and associated pre-cursor tap coefficients.
FIG. 5 is an simplified table of illustrative post-cursor tap values and associated post-cursor tap coefficients.

The CAUI-4 specification defines the functional model of the transmitter equalizer as a three tap transversal filter. An illustrative transmitter equalizer 300, which may represent a functional module of the transmitter equalizer implemented in each communication lane interface 212, 214, 216, 218 of the each chip-to-chip communication interface 210, is shown in FIG. 3. The transmitter equalizer 300 includes a pre-cursor tap $c(-1)$ 302, a cursor tap $c(0)$ 304, and a post-cursor tap $c(1)$ 306. In an illustrative embodiment, each set of filter tap settings identifies one of four possible tap values for the pre-cursor tap $c(-1)$ 302 using two bits and one of six possible tap values for the post-cursor tap $c(1)$ 306. For example, as shown in table 400 of FIG. 4, the pre-cursor tap value may be set to a value of "0" to select a pre-cursor tap $c(-1)$ coefficient of $0+/-0.04$, set to a value of "1" to select a pre-cursor tap $c(-1)$ coefficient of $-0.05+/-0.04$, set to a value of "2" to select a pre-cursor tap $c(-1)$ coefficient of $-0.1+/-0.04$, or set to a value of "3" to select a pre-cursor tap $c(-1)$ coefficient of $-0.15+/-0.04$. Similarly, as shown in table 500 of FIG. 5, the post-cursor tap value may be set to a value of "0" to select a post-cursor tap $c(1)$ coefficient of $0+/-0.04$, set to a value of "1" to select a post-cursor tap $c(1)$ coefficient of $-0.05+/-0.04$, set to a value of "2" to select a post-cursor tap $c(1)$ coefficient of $-0.1+/-0.04$, set to a value of "3" to select a post-cursor tap $c(1)$ coefficient of $-0.15+/-0.04$, set to a value of "4" to select a post-cursor tap $c(1)$ coefficient of $-0.2+/-0.04$, or set to a value of "5" to select a post-cursor tap $c(1)$ coefficient of $-0.25+/-0.04$. As such, in the illustrative embodiment, each set of filter tap coefficient settings may be embodied as five bits. The cursor tap $c(0)$ coefficient may be calculated based on the values of the other two tap coefficients, $c(-1)$ and $c(1)$, such that the equation: $c(0)-c(1)-c(-1)=1$, is satisfied.

The station management entity 202 may be embodied as any type of communication device or circuit capable of facilitating communications with the retimers 106 over the dedicated communication bus 120. As discussed above, the dedicated communication bus 120 is illustratively an MDIO bus, and the station management entity 202 may be embodied as an MDIO communication device. Although the station management entity 202 is illustrated in FIG. 2 as part of the communication controller 102, it should be appreciated that the station management entity 202 may be separate from, but communicatively coupled to, the communication controller 102 (e.g., the switch controller 200) in other embodiments. As discussed in more detail below, the station management entity 202 is configured to initialize and configure the filter equalization of the CAUI-4 transmitters of the chip-to-chip communication interfaces 210 of the communication system 100.

Figure 6:
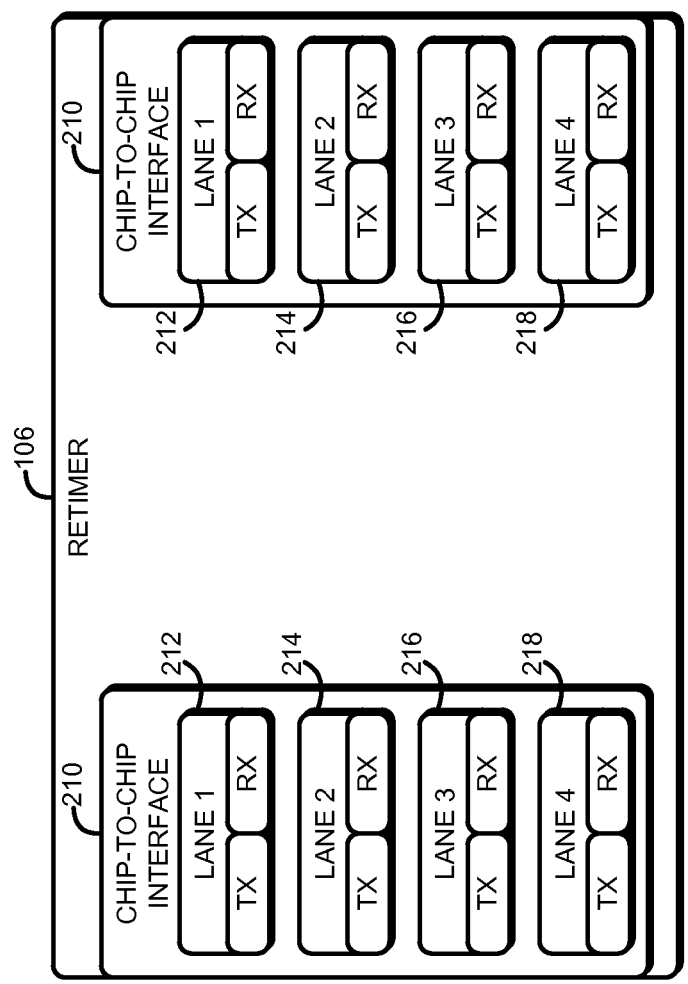
FIG. 6 is a simplified block diagram of at least one embodiment of a retimer of the communication system of FIG. 1.

Referring now to FIG. 6, each retimer 106 may include one or more chip-to-chip communication interfaces 210 similar to the chip-to-chip communication interfaces 210 of the switch controller 200. For example, in embodiments in which the retimer 106 is communicatively coupled to a module 104, the retimer 106 may include only one chip-to-chip communication interface 210. Alternatively, the retimer 106 may include two or more chip-to-chip communication interfaces 210, although only one or more of the chip-to-chip communication interfaces 210 may be used in a particular implementation (e.g., when the retimer 106 is communicatively coupled to a module 104). Of course, the retimer 106 may also include a chip-to-module communication interface (not shown) to facilitate communications between the retimer 106 and the module 104.

Figure 7:
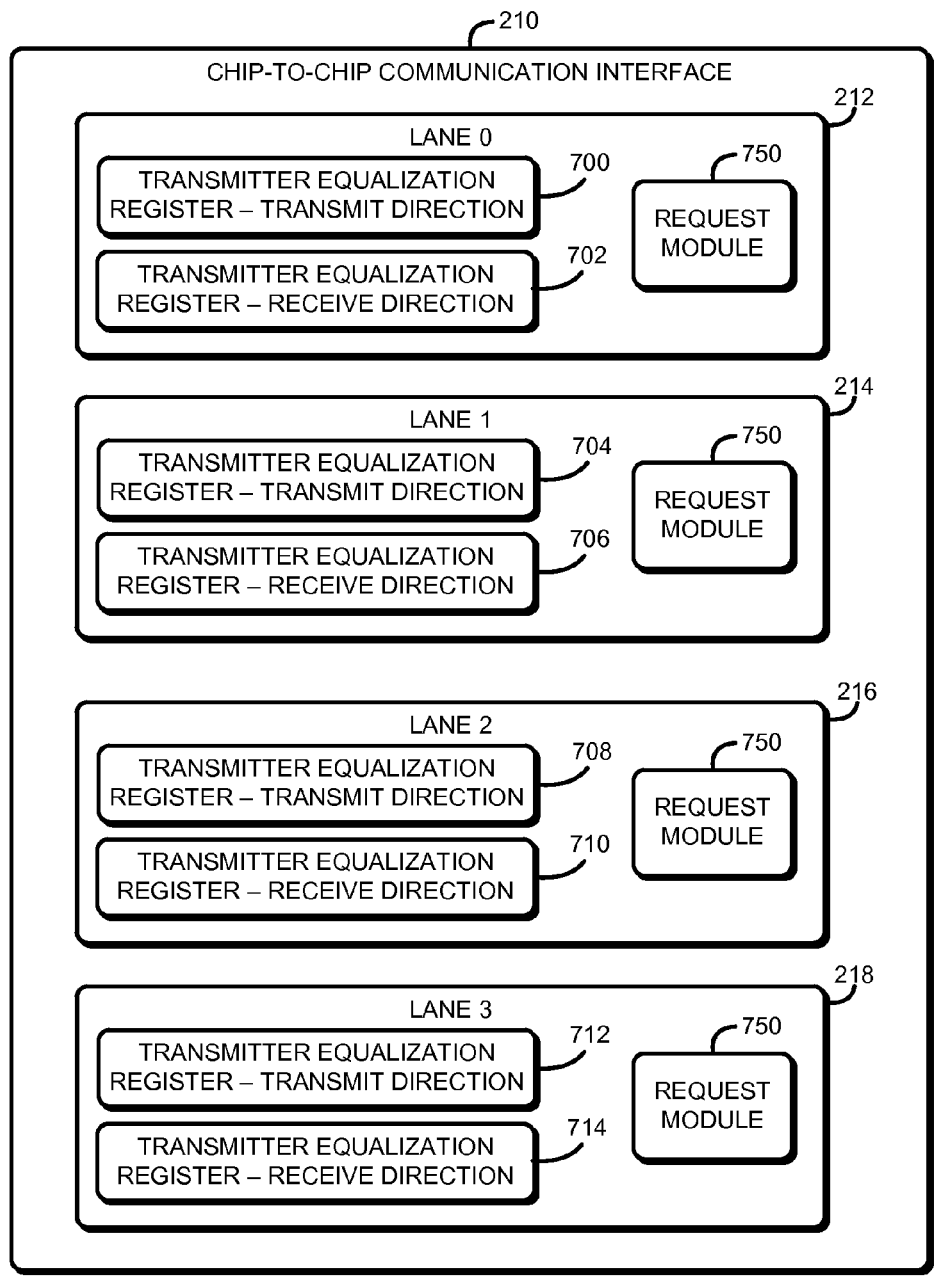
FIG. 7 is a simplified block diagram of at least one embodiment of a chip-to-chip communication interface of a switch controller of the communication controller of FIG. 2 and/or of the retimer of FIG. 3.

Referring now to FIG. 7, each chip-to-chip communication interface 210 of the communication devices of the system 100, including the switch controller 200 and each retimer 106, includes a plurality of communication lane interfaces. As discussed above, the illustrative chip-to-chip communication interfaces 210 are embodied as CAUI-4 chip-to-chip communication interfaces and, as such, each interface 210 includes four communication lane interfaces 212, 214, 216, 218. Each communication lane interface includes a transmitter equalization register for the transmit direction (700, 704, 708, 712) and a transmitter equalization register for the receive direction (702, 706, 710, 714). Illustratively, the transmit direction of the communication devices of the system 100 is defined as away from the communication controller 102 and the receive direction is defined as toward the communication controller 102. Of course, in other embodiments, other reference directions may be used.

In the illustrative embodiment, each communication lane interface 212, 214, 216, 218 also includes a request module 750, which may be embodied as software, firmware, hardware, or a combination thereof. For example, the request module 750 may be established by a processor other circuitry of the associated communication lane interface 212, 214, 216, 218, by a host processor of the associated communication device (e.g., the switch controller 200 or the retime 106, firmware or application software executed by the communication devices, or the like. In use, the request module 750 is configured to determine whether transmitter equalization is required by a receiver of the associated communication lane interface 212, 214, 216, 218. If transmitter equalization is desired, the request module 750 may set a request flag of the transmitter equalization register of the receiver of the associated communication lane interface 212, 214, 216, 218 and write the desired transmitter equalization settings to the transmitter equalization register of the receiver as discussed in more detail below.

As shown in FIG. 8, each transmitter equalization register 700, 702, 704, 706, 708, 710, 712, 714 of the chip-to-chip communication interface 210 has an associated address, which may be accessed to read and write to the transmitter equalization register. In the illustrative embodiment, the transmitter equalization register in the transmit direction 700 for the communication lane 0 interface 212 has an address of 1.184, the transmitter equalization register in the receive direction 702 for the communication lane 0 interface 212 has an address of 1.180, the transmitter equalization register in the transmit direction 704 for the communication lane 1 interface 214 has an address of 1.185, the transmitter equalization register in the receive direction 706 for the communication lane 1 interface 214 has an address of 1.181, the transmitter equalization register in the transmit direction 708 for the communication lane 2 interface 216 has an address of 1.186, the transmitter equalization register in the receive direction 710 for the communication lane 2 interface 216 has an address of 1.182, the transmitter equalization register in the transmit direction 712 for the communication lane 3 interface 218 has an address of 1.187, and the transmitter equalization register in the receive direction 714 for the communication lane 3 interface 218 has an address of 1.183. Of course, in other embodiments, other register addresses may be used for the transmitter equalization register 700, 702, 704, 706, 708, 710, 712, 714.

Referring now to FIG. 9, an illustrative transmitter equalization register 900 includes a request flag 902, a post-cursor request register bank 904, a pre-cursor request register bank 906, a post-cursor remote setting register bank 908, a pre-cursor remote setting register bank 910, a pre-cursor local setting register bank 914, and a pre-cursor local setting register bank 914. In the illustrative embodiment, each of the transmitter equalization registers 700, 702, 704, 706, 708, 710, 712, 714 discussed above is embodied as a transmitter equalization register 900.

Figure 11:

As discussed in more detail below, the request flag 902 is used by a receiver of a communication lane interface 212, 214, 216, 218 to request transmitter equalization of the corresponding lane transmitter of its partner communication device. As shown in FIG. 10, the request flag 902 is illustratively embodied as bit 15 of the transmitter equalization register 900. Additionally, as shown in FIG. 11, by setting the request flag to true, the receiver may request a change to the partner transmitter equalization. Similarly, by setting the request flag to false, the receiver may indicate that no transmitter equalization is needed for that particular lane and transmit direction.

The post-cursor request register bank 904 and the pre-cursor request register bank 906 may be used by a receiver of a communication lane interface to indicate the desired transmitter equalization settings. To do so, in addition to setting the request flag 902, the request module 750 of the associated communication lane interface 212, 214, 216, 218 may write the desired post-cursor $c(1)$ and pre-cursor $c(-1)$ tap values to the corresponding post-cursor request register bank 904 and pre-cursor request register bank 906. As shown in FIG. 10, the post-cursor request register bank 904 is illustratively embodied as bits 14, 13, and 12 of the transmitter equalization register 900, and the pre-cursor request register bank 906 is illustratively embodied as bits 11 and 10 of the transmitter equalization register 900.

As shown in FIG. 11, the request module 750 may write a binary "000" to the post-cursor request register bank 904 to set the associated variable Requested_eq_c1 to a value of "0", which selects a post-cursor tap value of 0 and an associated post-cursor tap $c(1)$ coefficient of 0+/−0.04; a binary "001" to the post-cursor request register bank 904 to set the associated variable Requested_eq_c1 to a value of "1", which selects a post-cursor tap value of 1 and an associated post-cursor tap $c(1)$ coefficient of −0.05+/−0.04; a binary "010" to the post-cursor request register bank 904 to set the associated variable Requested_eq_c1 to a value of "2", which selects a post-cursor tap value of 2 and an associated post-cursor tap $c(1)$ coefficient of −0.1+/−0.04; a binary "011" to the post-cursor request register bank 904 to set the associated variable Requested_eq_c1 to a value of "3", which selects a post-cursor tap value of 3 and an associated post-cursor tap $c(1)$ coefficient of −0.15+/−0.04; a binary "100" to the post-cursor request register bank 904 to set the associated variable Requested_eq_c1 to a value of "4", which selects a post-cursor tap value of 4 and an associated post-cursor tap $c(1)$ coefficient of −0.2+/−0.04; or a binary "101" to the post-cursor request register bank 904 to set the associated variable Requested_eq_c1 to a value of "5", which selects a post-cursor tap value of 5 and an associated post-cursor tap $c(1)$ coefficient of −0.25+/−0.04.

Similarly, the request module 750 may write a binary "00" to the pre-cursor request register bank 906 to set the associated variable Requested_eq_cm1 to a value of "0", which selects a pre-cursor tap value of 0 and an associated pre-cursor tap $c(1)$ coefficient of 0+/−0.04; a binary "01" to the pre-cursor request register bank 906 to set the associated variable Requested_eq_c1 to a value of "1", which selects a pre-cursor tap value of 1 and an associated pre-cursor tap $c(1)$ coefficient of −0.05+/−0.04; a binary "10" to the pre-cursor request register bank 906 to set the associated variable Requested_eq_c1 to a value of "2", which selects a pre-cursor tap value of 2 and an associated pre-cursor tap $c(1)$ coefficient of −0.1+/−0.04; or a binary "11" to the pre-cursor request register bank 906 to set the associated variable Requested_eq_c1 to a value of "3", which selects a pre-cursor tap value of 3 and an associated pre-cursor tap $c(1)$ coefficient of −0.15+/−0.04.

The post-cursor remote setting register bank 908 and the pre-cursor remote setting register bank 910 are used by a receiver of a communication lane interface 212, 214, 216, 218 to store the current transmitter equalization settings used by the partner transmitter of the corresponding communication lane. The value stored in the post-cursor remote setting register bank 908 and pre-cursor remote setting register bank 910 is indicative of the coefficient of the post-cursor tap $c(-1)$ and pre-cursor tap $c(1)$, respectively, used by the partner transmitter. In use, as discussed in more detail below, the station management entity 202 reads the post-cursor setting value and pre-cursor setting value of the partner transmitter and writes those values to the post-cursor remote setting register bank 908 and pre-cursor remote setting register bank 910 of the receiver. As shown in FIG. 10, the post-cursor remote setting register bank 908 is illustratively embodied as bits 9, 8, and 7 of the transmitter equalization register 900, and the pre-cursor request register bank 906 is illustratively embodied as bits 6 and 5 of the transmitter equalization register 900.

As shown in FIG. 11, the station management entity 202 may write a binary "000" to the post-cursor remote setting register bank 908 to set the associated variable Remote_eq_c1 to a value of "0", which sets the post-cursor tap value to 0 and indicates the associated post-cursor tap $c(1)$ coefficient is 0+/−0.04; a binary "001" to the post-cursor remote setting register bank 908 to set the associated variable Remote_eq_c1 to a value of "1", which sets the post-cursor tap value to 1 and indicates the associated post-cursor tap $c(1)$ coefficient is −0.5+/−0.04; a binary "010" to the post-cursor remote setting register bank 908 to set the associated variable Remote_eq_c1 to a value of "2", which sets the post-cursor tap value to 2 and indicates the associated post-cursor tap $c(1)$ coefficient is −0.1+/−0.04; a binary "011" to the post-cursor remote setting register bank 908 to set the associated variable Remote_eq_c1 to a value of "3", which sets the post-cursor tap value to 3 and indicates the associated post-cursor tap $c(1)$ coefficient is −0.15+/−0.04; a binary "100" to the post-cursor remote setting register bank 908 to set the associated variable Remote_eq_c1 to a value of "4", which sets the post-cursor tap value to 4 and indicates the associated post-cursor tap $c(1)$ coefficient is −0.2+/−0.04; a binary "101" to the post-cursor remote setting register bank 908 to set the associated variable Remote_eq_c1 to a value of "5", which sets the post-cursor tap value to 5 and indicates the associated post-cursor tap $c(1)$ coefficient is −0.25+/−0.04.

Similarly, the station management entity 202 may write a binary "00" to the pre-cursor request register bank 906 to set the associated variable Remote_eq_cm1 to a value of "0", which sets the pre-cursor tap value to 0 and indicates the associated pre-cursor tap $c(1)$ coefficient is 0+/−0.04; a binary "01" to the pre-cursor request register bank 906 to set the associated variable Remote_eq_cm1 to a value of "0", which sets the pre-cursor tap value to 0 and indicates the associated pre-cursor tap $c(1)$ coefficient is 0+/−0.04; a binary "10" to the pre-cursor request register bank 906 to set the associated variable Remote_eq_cm1 to a value of "0", which sets the pre-cursor tap value to 0 and indicates the associated pre-cursor tap $c(1)$ coefficient is 0+/−0.04; or a binary "11" to the pre-cursor request register bank 906 to set the associated variable Remote_eq_cm1 to a value of "0", which sets the pre-cursor tap value to 0 and indicates the associated pre-cursor tap $c(1)$ coefficient is 0+/−0.04.

As shown in FIG. 11, the post-cursor local setting 912 and the pre-cursor local setting 914 are used by the transmitter of a communication lane interface 212, 214, 216, 218 to control the transmitter equalization of that transmitter. The value stored in the post-cursor local setting register bank 912 and pre-cursor local setting register bank 914 is indicative of the coefficient of the post-cursor tap $c(-1)$ and pre-cursor tap $c(1)$, respectively, used by the transmitter. In use, as discussed in more detail below, the station management entity 202 reads and writes to the post-cursor local setting 912 and the pre-cursor local setting 914 to perform the transmitter equalization for a particular communication lane. As shown in FIG. 10, the post-cursor local setting register bank 912 is illustratively embodied as bits 4, 3, and 2 of the transmitter equalization register 900, and the pre-cursor local setting register bank 914 is illustratively embodied as bits 1 and 0 of the transmitter equalization register 900.

Additionally, as shown in FIG. 11, the station management entity 202 may write a binary "000" to the post-cursor local setting register bank 912 to set the associated variable $Local_{13}$ eq_c1 to a value of "0", which selects a post-cursor tap value of 0 and an associated post-cursor tap c(1) coefficient of 0+/−0.04; a binary "001" to the post-cursor local setting register bank 912 to set the associated variable $Local_{13}eq_{13}c1$ to a value of "1", which selects a post-cursor tap value of 1 and an associated post-cursor tap c(1) coefficient of −0.05+/−0.04; a binary "010" to the post-cursor local setting register bank 912 to set the associated variable Local_eq_c1 to a value of "2", which selects a post-cursor tap value of 2 and an associated post-cursor tap c(1) coefficient of −0.1+/−0.04; a binary "011" to the post-cursor local setting register bank 912 to set the associated variable Local_eq_c1 to a value of "3", which selects a post-cursor tap value of 3 and an associated post-cursor tap c(1) coefficient of −0.15+/−0.04; a binary "100" to the post-cursor local setting register bank 912 to set the associated variable Local_eq_c1 to a value of "4", which selects a post-cursor tap value of 4 and an associated post-cursor tap c(1) coefficient of −0.2+/−0.04; a binary "101" to the post-cursor local setting register bank 912 to set the associated variable Remote_eq_c1 to a value of "5", which selects a post-cursor tap value of 5 and an associated post-cursor tap c(1) coefficient of −0.25+/−0.04.

Similarly, the station management entity 202 may write a binary "00" to the pre-cursor local setting register bank 914 to set the associated variable Local_eq_cm1 to a value of "0", which selects a pre-cursor tap value of 0 and an associated post-cursor tap c(1) coefficient of 0+/−0.04; a binary "01" to the pre-cursor local setting register bank 914 to set the associated variable Local_eq_cm1 to a value of "1", which selects a pre-cursor tap value of 1 and an associated post-cursor tap c(1) coefficient of −0.5+/−0.04; a binary "10" to the pre-cursor local setting register bank 914 to set the associated variable Local_eq_cm1 to a value of "2", which selects a pre-cursor tap value of 2 and an associated post-cursor tap c(1) coefficient of −0.1+/−0.04; a binary "11" to the pre-cursor local setting register bank 914 to set the associated variable Local_eq_cm1 to a value of "2", which selects a pre-cursor tap value of 2 and an associated post-cursor tap c(1) coefficient of −0.15+/−0.04.

Figure 13:
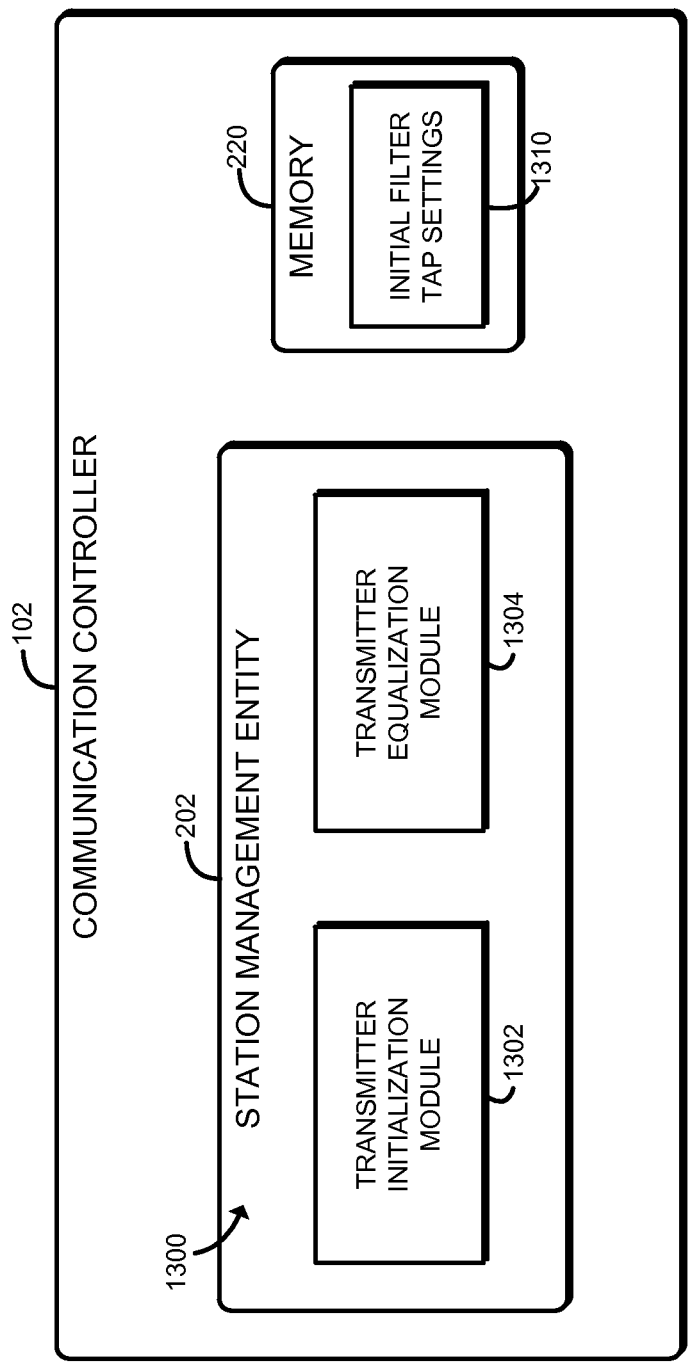
FIG. 13 is a simplified block diagram of at least one embodiment of an environment of a station management entity of the communication controller of FIG. 2.

Referring now to FIG. 13, in use, the station management entity 202 establishes an environment 1300. The illustrative environment 1300 includes a transmitter initialization module 1302 and a transmitter equalization module 1304. Each of the modules 1302, 1304 may be embodied as hardware, firmware, software, or a combination thereof. The transmitter initialization module 1302 is configured to retrieve initial transmitter equalization settings 1310 for each transmitter of each controlled CAUI-4 chip-to-chip communication interface 210 of the system 100 from the memory 220. As discussed in more detail below, the transmitter initialization module 1302 is configured to write the initial transmitter equalization settings 1310 to the transmitter equalization registers 900 of the communication lane interfaces 212, 214, 216, 218. In this way, each transmitter of each communication lane interface 212, 214, 216, 218 may be initialized from a central storage of initial transmitter equalization settings 1310.

The transmitter equalization module 1304 is configured to perform transmitter equalization for each pair of communication lane interfaces 212, 214, 216, 218 of each communication lane. To do so, as discussed in more detail below, the transmitter equalization module 1304 reads the present transmitter equalization settings for each transmitter of each communication lane interface 212, 214, 216, 218 and write the current transmitter filter tap settings to the transmitter equalization register 900 of the corresponding receiver, such that the receiver has knowledge of the present settings. To do so, the transmitter equalization module 1304 may read the post-cursor local setting register bank 912 and the pre-cursor local setting register bank 914 of each transmitter to retrieve the and write the transmitter equalization settings to the post-cursor remote setting register bank 908 and the pre-cursor remote setting register bank 910 of the corresponding receiver, respectively. Additionally, the transmitter equalization module 1304 may determine whether the corresponding receiver has requested transmitter equalization by checking the request flag of the transmitter equalization register 900 of the corresponding receiver and reading the requested transmitter equalization settings from the post-cursor request register bank 904 and the pre-cursor request register bank 906. The transmitter equalization module 1304 may then write the requested transmitter equalization settings to the post-cursor local setting register bank 912 and the pre-cursor local setting register bank 914 of the transmitter equalization register of the corresponding transmitter to set the transmitter equalization settings of the transmitter. The transmitter equalization module 1304 may repeat the described process for the other transmitter-receiver pair (i.e., for the opposite communication direction) for the present communication lane and the transmitter-receiver pairs for any remaining communication lane interfaces 212, 214, 216, 218.

Figure 14:
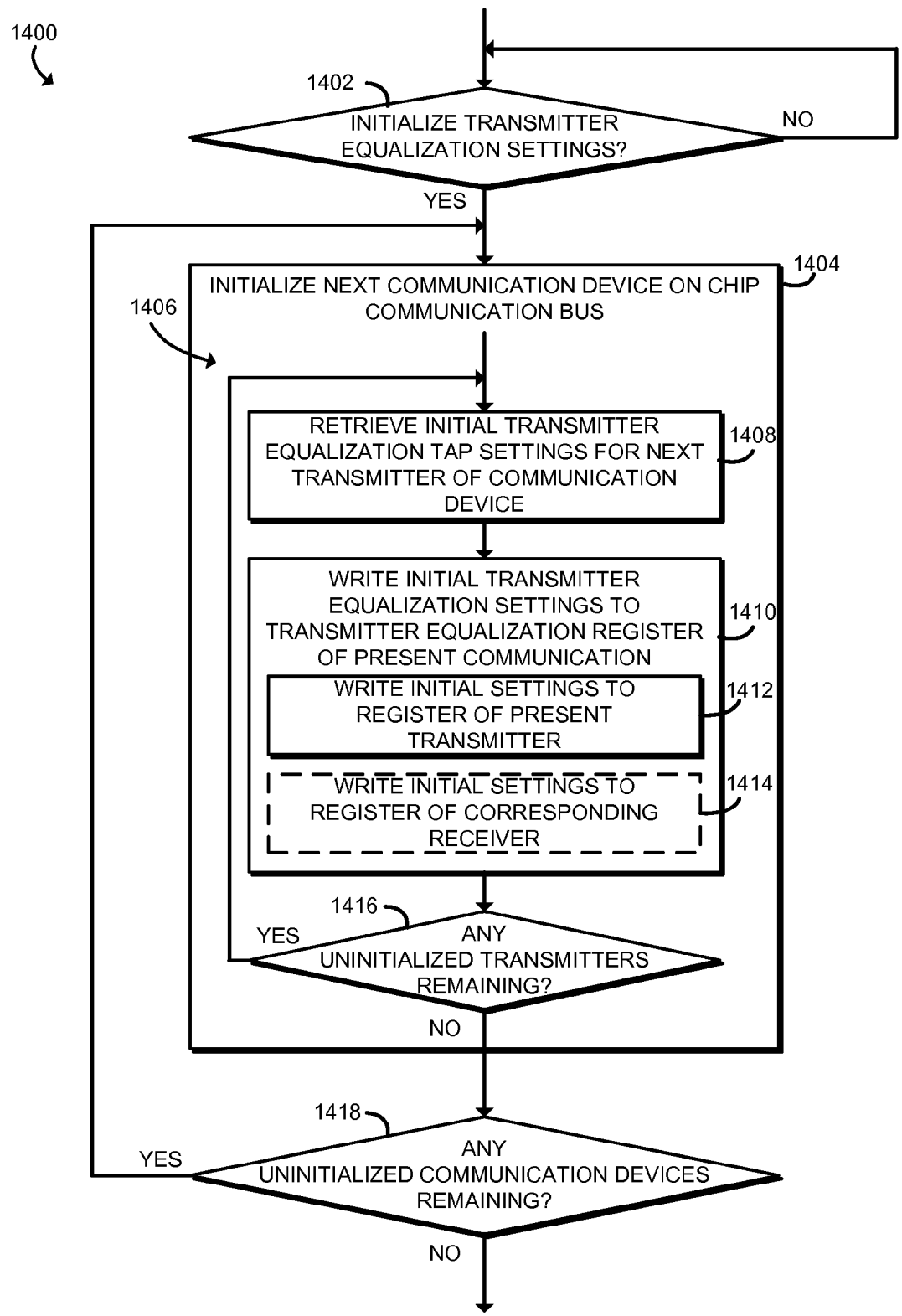
FIG. 14 is a simplified flow diagram of at least one embodiment of a method for initializing transmitter equalization settings of communication devices of the communication system of FIG. 1.

Referring now to FIG. 14, in use, the station management entity 202 may execute a method 1400 to initialize the transmitter equalization settings of communication devices (e.g., the switch controller 200 and/or retimers 106) of the communication system 100. The method 1400 begins with block 1402 in which the station management entity 202 determines whether initialization of the transmitter equalization settings is required. If so, the method 1400 advances to block 1404 in which the transmitter equalization settings of the next communication device on the dedicated communication bus 120 is initialized.

To do so, the station management entity 202 may execute a sub-method 1406 to initialize the transmitter equalization settings of each communication device. The sub-method 1406 begins with bock 1408 in which the station management entity 202 reads the initial transmitter equalization settings for the next transmitter of the present communication device from the memory 220. As discussed above, each CAUI-4 chip-to-chip communication interface 210 of the present communication device includes four lanes, each having an associated transmitter. In block 1410, the station management entity 202 writes the initial transmitter equalization settings to the transmitter equalization register 900 of the present transmitter. To do so, the station management entity 202 may write the initial transmitter equalization settings to the post-cursor local setting register bank 912 (i.e., the post-cursor tap c(1) value) and the pre-cursor local setting register bank 914 (i.e., the pre-cursor tap c(−1) value) in block 1412. Additionally, in some embodiments, the station management entity 202 may write the initial transmitter equalization settings for the present transmitter to the transmitter equalization register 900 of the paired receiver of the present transmitter. To do so, the station management entity 202 may write the initial transmitter equalization settings to the post-cursor remote setting register bank 908 and the pre-cursor remote setting register bank 910 of the transmitter equalization register 900 of the corresponding receiver.

Subsequently, in block 1416, the station management entity 202 determines whether there are any remaining uninitialized transmitters in the present communication device. If there are uninitialized transmitters remaining, the sub-method 1406 loops back to block 1408 in which the initial transmitter equalization settings for the next transmitter of the present communication device is retrieved from the memory 220. However, if there are no uninitialized transmitters remaining in the present communication device, the sub-method 1406 advances to block 1418. In block 1418, the station management entity 202 determines whether there are any communication devices on the dedicated communication bus 120 that have not yet been initialized. If so, the method 1400 loops back to block 1404 in which the next uninitialized communication device of the dedicated communication bus 120 is initialized.

Figure 15:
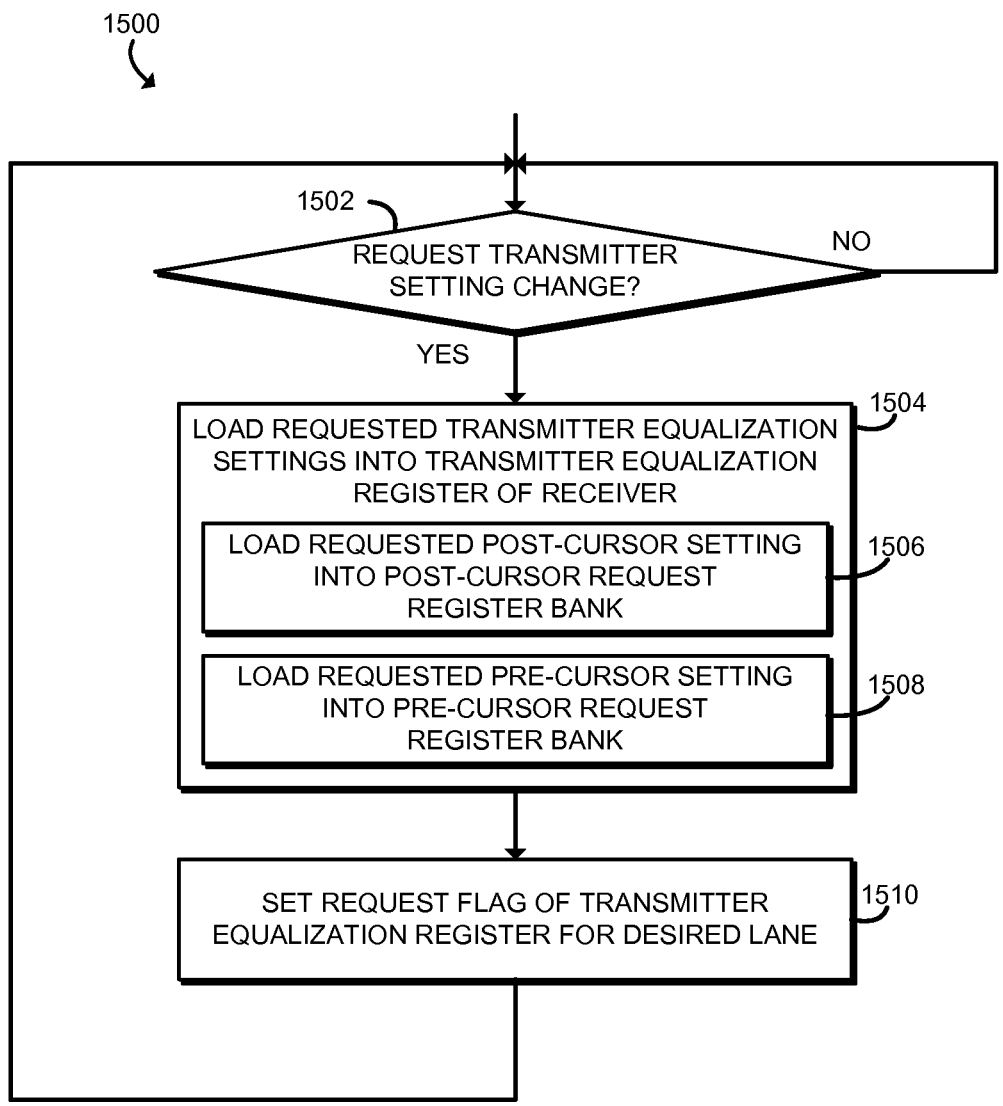
FIG. 15 is a simplified flow diagram of at least one embodiment of a method for requesting transmitter equalization that may be executed by a receiver of the chip-to-chip communication interface of FIG. 7.

Referring now to FIG. 15, in use, each communication device of the system 100 may execute a method 1500 to request transmitter equalization. For example, the method 1500 may be executed by a receiver of a communication lane interface 212, 214, 216, 218 (e.g., the request module 750) of any of the devices of the system 100. The method 1500 begins with block 1502 in which the receiver determines whether a change to the present transmitter equalization settings is desired or required. If so, the method 1500 advances to block 1504 in which the receiver loads the requested transmitter equalization register in the transmitter equalization register 900 of the receiver. To do so, the receiver may load the requested setting for the post-cursor tap c(1) 306 into the post-cursor request register bank 904 of its transmitter equalization register 900 in block 1506. Additionally, the receiver may load the requested setting for the pre-cursor tap c(−1) 302 into the pre-cursor request register bank 906 in block 1508.

Subsequently, in block 1510, the receiver may set the request flag 902 of the transmitter equalization register 900 to indicate that an equalization change is requested. The method then loops back to block 1502 in which the receiver may monitor the transmitter equalization settings to determine if further adjustments are needed at a later time.

Figure 16:
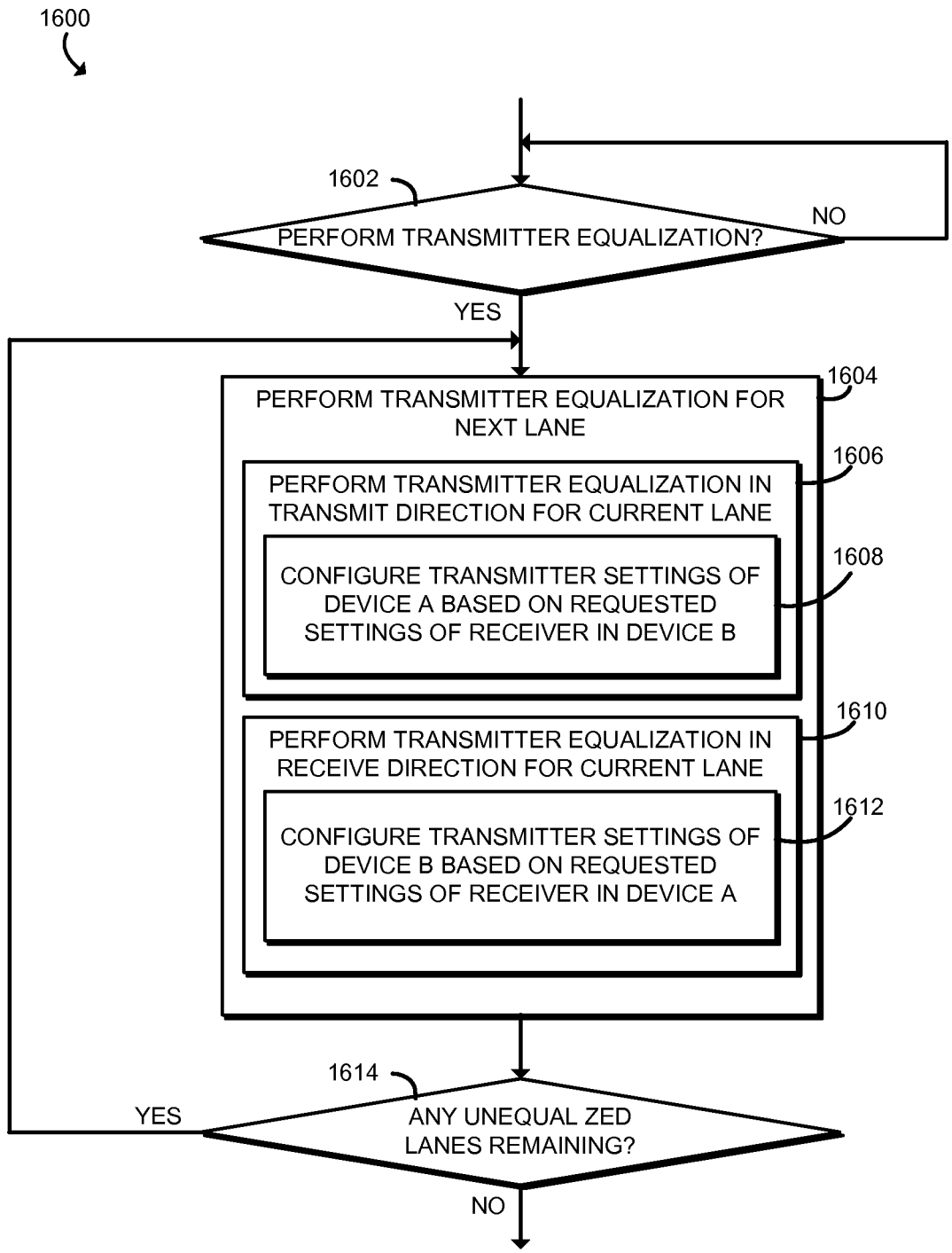
FIG. 16 is a simplified flow diagram of at least one embodiment of a method for performing transmitter equalization that may be executed by the station management entity of the communication controller of FIG. 13.

Referring now to FIG. 16, in use, the station management entity 202 may execute a method 1600 for performing transmitter equalization of the communication devices (e.g., the switch controller 200 and/or retimers 106) on the dedicated communication bus 120. The method 1600 begins with block 1602 in which the station management entity 202 determines whether to perform transmitter equalization for a pair of communication devices ("communication device A" and "communication device B") on the dedicated communication bus. If so, the method 1600 advances to block 1600 in which the station management entity 202 performs transmitter equalization for both transmitter-receiver pairs of the next communication lane of the pair of communication devices for which transmitter equalization is being performed.

To do so, in block 1606, the station management entity 202 performs transmitter equalization in the transmit direction for the current communication lane. For example, in block 1608, the station management entity 202 configures the transmitter settings of communication device A of the present communication device pair based on the requested settings of the corresponding receiver in communication device B of the present communication device pair. Subsequently, in block 1610, the station management entity 202 performs transmitter equalization in the receive direction for the current communication lane. For example, in block 1612, the station management entity 202 configures the transmitter settings of communication device B of the present communication device pair based on the requested settings of the corresponding receiver in communication device A of the present communication device pair.

Figure 17:
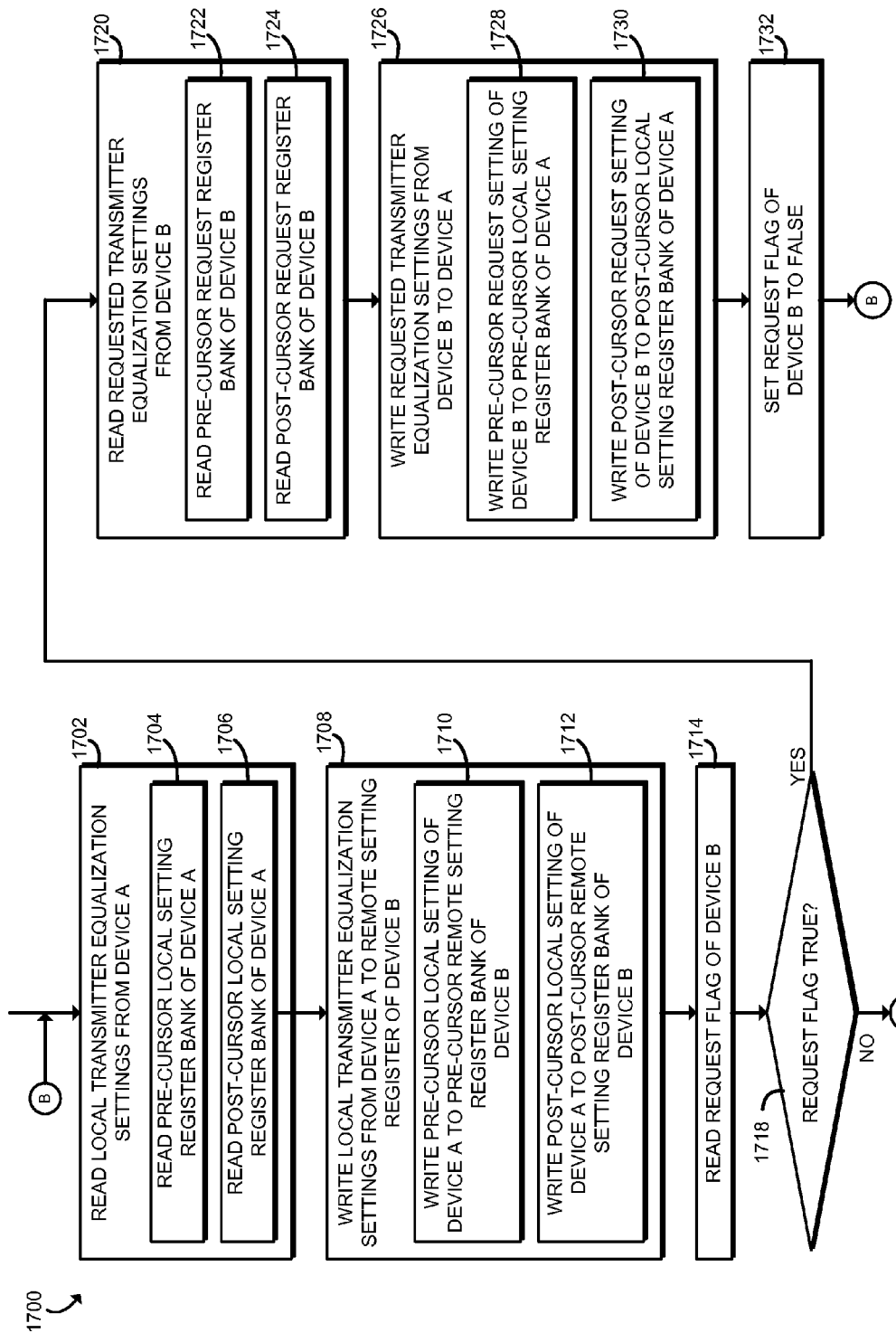
FIGS. 17 and 18 are a simplified flow diagram of at least one embodiment of a method for performing transmitter equalization for a communication lane of two communication devices.

Referring now to FIG. 17, in an illustrative embodiment, the station management entity 202 may execute a method 1700 to perform the transmitter equalization of block 1604 of method 1600 for a single communication lane of a pair of communication devices ("communication device A" and "communication device B"). In the illustrative embodiment, the communication device A is selected as the communication device closest to the station management entity, but other configurations may be used in other embodiments. The method 1700 begins with block 1702 in which the station management entity 202 reads the local transmitter equalization settings from the transmitter equalization register 900 of the transmitter of the communication device A. To do so, the station management entity 202 reads the pre-cursor local setting register bank 914 of the transmitter equalization register 900 of the transmitter of the communication device A in block 1704 and reads the post-cursor local setting register bank 912 of the transmitter equalization register 900 of the transmitter of the communication device A in block 1706.

In block 1708, the station management entity 202 writes the local transmitter equalizations settings read from the communication device A to the transmitter equalization register 900 of the corresponding partner receiver of the communication device B. To do so, the station management entity 202 writes the pre-cursor local setting read in block 1704 to the pre-cursor remote setting register bank 910 of the transmitter equalization register 900 of the partner receiver of the communication device B in block 1710. Additionally, in block 1712, the station management entity 202 writes the post-cursor local setting read in block 1706 to the post-cursor remote setting register bank 908 of the transmitter equalization register 900 of the partner receiver of the communication device B.

Subsequently, in block 1714, the station management entity reads the request flag 902 of the transmitter equalization register 900 of the partner receiver of the communication device B. As discussed above, the partner receiver of the communication device B may set the request flag to request transmitter equalization of the partner transmitter. If the request flag has been set (e.g., set to "true") by the partner receiver as determined in block 1718, the method 1700 advances to block 1720 in which the station management entity 202 reads the requested transmitter equalization settings from the transmitter equalization register 900 of the partner receiver of the communication device B. To do so, the station management entity 202 reads the pre-cursor request register bank 906 of the transmitter equalization register 900 of the partner receiver of the communication device B in block 1722 and reads the post-cursor request register bank 904 of the transmitter equalization register 900 of the partner receiver of the communication device B in block 1724.

In block 1726, the station management entity 202 writes the requested transmitter equalizations settings read from the communication device B to the transmitter equalization register 900 of the corresponding partner transmitter of the communication device A. To do so, the station management entity 202 writes the pre-cursor request setting read in block 1722 to the pre-cursor local setting register bank 914 of the transmitter equalization register 900 of the partner transmitter of the communication device A in block 1728. Additionally, in block 1730, the station management entity 202 writes the post-cursor local setting read in block 1724 to the post-cursor local setting register bank 912 of the transmitter equalization register 900 of the partner transmitter of the communication device A.

Subsequently, in block 1732, the request flag 902 of the transmitter equalization register 900 of the partner receiver of the communication device B is set to false. In some embodiments, the partner receiver may set the request flag 902 to false to indicate that no further transmitter equalization is required. In other embodiments, the station management entity 202 may set the request flag 902 to false to indicate that the transmitter equalization has been performed. Regardless, the method 1700 loops back to block 1702 in which the local transmitter equalization settings of the partner transmitter of the communication device A are read again and subsequently written to the remote setting register banks 908, 810 of the transmitter equalization register 900 of the partner receiver of communication device B in block 1708.

Figure 18:
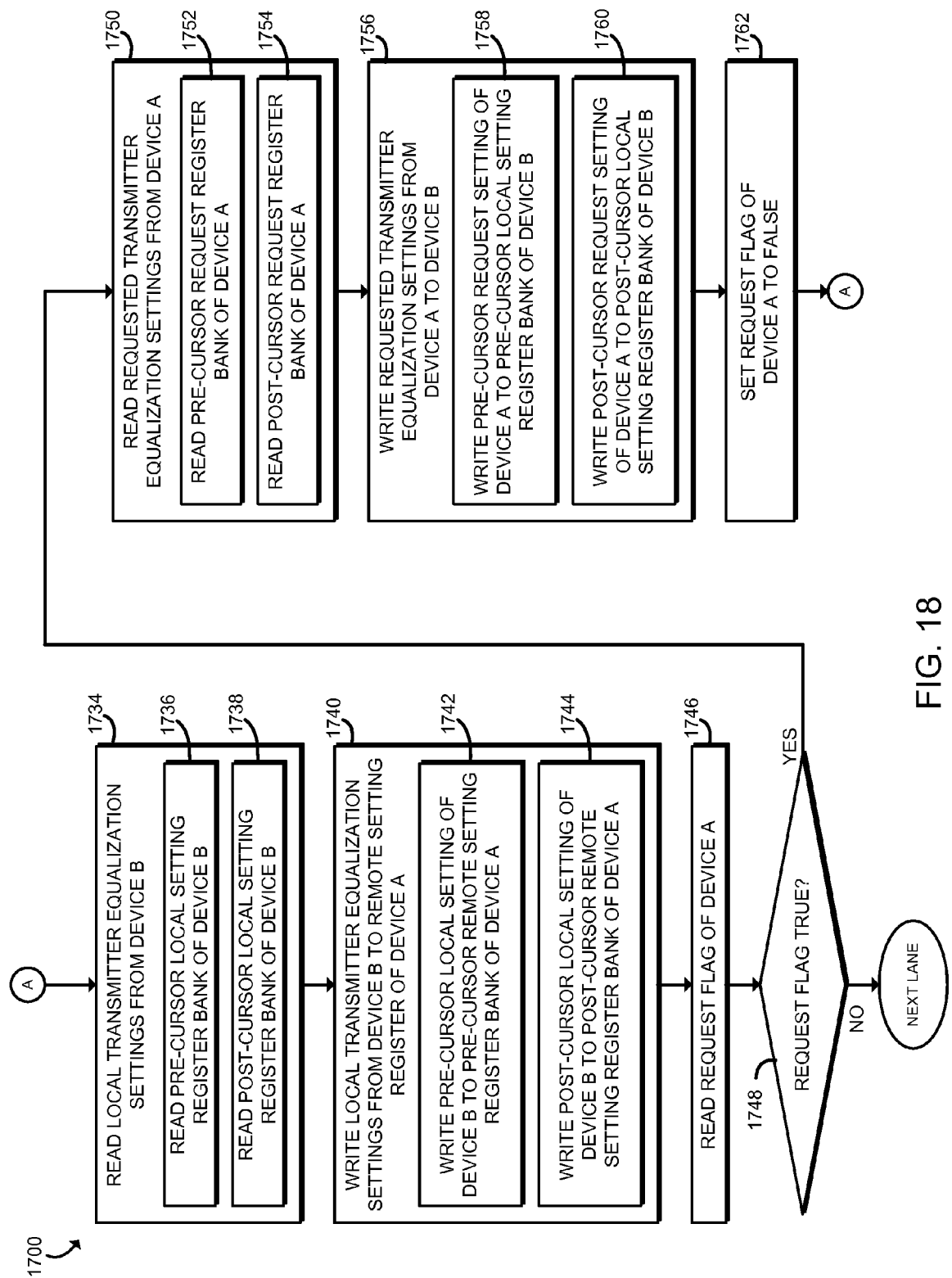

In block 1714, the station management entity 202 again reads the request flag 902 of the transmitter equalization register 900 of the partner receiver of the communication device B. In block 1718, the station management entity 202 again determines whether the request flag 902 is "true" or "false." If the station management entity 202 now determines that the request flag 902 of the transmitter equalization register 900 is "false," the method 1700 advances to block 1734 of FIG. 18. In block 1734, the station management entity 202 reads the local transmitter equalization settings from the transmitter equalization register 900 of the transmitter of the communication device B. To do so, the station management entity 202 reads the pre-cursor local setting register bank 914 of the transmitter equalization register 900 of the transmitter of the communication device B in block 1736 and reads the post-cursor local setting register bank 912 of the transmitter equalization register 900 of the transmitter of the communication device B in block 1738.

In block 1740, the station management entity 202 writes the local transmitter equalizations settings read from the communication device B to the transmitter equalization register 900 of the corresponding partner receiver of the communication device A. To do so, the station management entity 202 writes the pre-cursor local setting read in block 1734 to the pre-cursor remote setting register bank 910 of the transmitter equalization register 900 of the partner receiver of the communication device A in block 1742. Additionally, in block 1744, the station management entity 202 writes the post-cursor local setting read in block 1736 to the post-cursor remote setting register bank 908 of the transmitter equalization register 900 of the partner receiver of the communication device A.

Subsequently, in block 1746, the station management entity 202 reads the request flag 902 of the transmitter equalization register 900 of the partner receiver of the communication device A. As discussed above, the partner receiver of the communication device A may set the request flag to request transmitter equalization of the partner transmitter. If the request flag has been set (e.g., set to "true") by the partner receiver as determined in block 1748, the method 1700 advances to block 1750 in which the station management entity 202 reads the requested transmitter equalization settings from the transmitter equalization register 900 of the partner receiver of the communication device A. To do so, the station management entity 202 reads the pre-cursor request register bank 906 of the transmitter equalization register 900 of the partner receiver of the communication device A in block 1752 and reads the post-cursor request register bank 904 of the transmitter equalization register 900 of the partner receiver of the communication device A in block 1754.

In block 1756, the station management entity 202 writes the requested transmitter equalizations settings read from the communication device A to the transmitter equalization register 900 of the corresponding partner transmitter of the communication device B. To do so, the station management entity 202 writes the pre-cursor request setting read in block 1752 to the pre-cursor local setting register bank 914 of the transmitter equalization register 900 of the partner transmitter of the communication device B in block 1758. Additionally, in block 1760, the station management entity 202 writes the post-cursor local setting read in block 1754 to the post-cursor local setting register bank 912 of the transmitter equalization register 900 of the partner transmitter of the communication device B.

Subsequently, in block 1762, the request flag 902 of the transmitter equalization register 900 of the partner receiver of the communication device A is set to false. As discussed above, the partner receiver may set the request flag 902 to false to indicate that no further transmitter equalization is required and/or the station management entity 202 may set the request flag 902 to false to indicate that the transmitter equalization has been performed. Regardless, the method 1700 subsequently loops back to block 1734 in which the local transmitter equalization settings of the partner transmitter of the communication device B are read again and subsequently written to the remote setting register banks 908, 810 of the transmitter equalization register 900 of the partner receiver of communication device A in block 1740.

In block 1746, the station management entity 202 again reads the request flag 902 of the transmitter equalization register 900 of the partner receiver of the communication device A. In block 1748, the station management entity 202 again determines whether the request flag 902 is "true" or "false." If the station management entity 202 now determines that the request flag 902 of the transmitter equalization register 900 is "false," the station management entity 202 has completed the transmitter equalization of the present communication lane and may continue on to the next communication lane and corresponding pair of communication devise A and B.

Referring back to FIG. 15, after the station management entity 202 has performed transmitter equalization for the present communication lane, the method 1600 advances to block 1614. In block 1614, the station management entity 202 determines whether any un-equalized communication lanes remain. If so, the method 1600 loops back to block 1604 to perform transmitter equalization for the next communication lane (i.e., on the next pair of communication devices A and B). The station management entity 202 may perform transmitter equalization this way on each communication lane for each pair of communication devices of the system 100.

It should be further appreciated that the particular blocks of the methods 1500, 1600, 1700 may be executed in a sequential order other than that described above. Additionally, one or more of the blocks of the methods 1500, 1600, 1700 may be executed in parallel with one or more other blocks of the same method. Additionally, in some embodiments, time-outs or delays may be used in the method 1500, 1600, and/or 1700.

EXAMPLES

Illustrative examples of the devices, systems, and methods disclosed herein are provided below. An embodiment of the devices, systems, and methods may include any one or more, and any combination of, the examples described below.

Example 1 includes a station management entity of a communication controller of a communication system for performing transmitter equalization, the station management entity comprising a transmitter equalization module to read, via a dedicated communication bus established between the station management entity and a plurality of communication devices of the communication system, local transmitter equalization settings from a first transmitter equalization register of a first communication lane interface of a first communication device; and write, via the dedicated communication bus, the local transmitter equalization settings of the first communication lane interface of the first communication device to a first transmitter equalization register of a first communication lane interface of a second communication device, wherein the first communication lane interface of the first communication device is communicatively coupled with the first communication lane interface of the second communication device via a chip-to-chip communication link different from the dedicated communication bus.

Example 2 includes the subject matter of Example 1, and wherein the dedicated communication bus comprises a management data input/output (MDIO) bus, the local transmitter equalization settings.

Example 3 includes the subject matter of any of Examples 1 and 2, and wherein to read the local transmitter equalization settings comprises to read a pre-cursor local value from a pre-cursor local setting register bank of the first transmitter equalization register of the first communication lane interface of the first communication device, and read a post-cursor local value from a post-cursor local setting register bank of the first transmitter equalization register of the first communication lane interface of the first communication device.

Example 4 includes the subject matter of any of Examples 1-3, and wherein the pre-cursor local setting register bank comprises bits 0 and 1 of first transmitter equalization register of the first communication lane interface of the first communication device, and the post-cursor local setting register bank comprises bits 2, 3, and 4 of the first transmitter equalization register of the first communication lane interface of the first communication device.

Example 5 includes the subject matter of any of Examples 1-4, and wherein the transmitter equalization module is further to write the pre-cursor local value to a pre-cursor remote setting register bank of the first transmitter equalization register of the first communication lane interface of the second communication device; and write the post-cursor local value to a post-cursor remote setting register bank of the first transmitter equalization register of the first communication lane interface of the second communication device.

Example 6 includes the subject matter of any of Examples 1-5, and wherein the pre-cursor remote setting register bank comprises bits 5 and 6 of the first transmitter equalization register of the first communication lane interface of the second communication device, and the post-cursor remote setting register bank comprises bits 7, 8, and 9 of the first transmitter equalization register of the first communication lane interface of the second communication device.

Example 7 includes the subject matter of any of Examples 1-6, and wherein the first transmitter equalization register of the first communication lane interface of the first communication device has an address of 1.180, 1.181, 1.182, 1.183, 1.184, 1.185, 1.186, or 1.87.

Example 8 includes the subject matter of any of Examples 1-7, and wherein the first transmitter equalization register of the first communication lane interface of the second communication device has an address of 1.180, 1.181, 1.182, 1.183, 1.184, 1.185, 1.186, or 1.87.

Example 9 includes the subject matter of any of Examples 1-8, and wherein the transmitter equalization module is further to read, via the dedicated communication bus, a request flag from the first transmitter equalization register of the first communication lane interface of the second communication device.

Example 10 includes the subject matter of any of Examples 1-9, and wherein the request flag comprises bit 15 of the first transmitter equalization register of the first communication lane interface of the second communication device.

Example 11 includes the subject matter of any of Examples 1-10, and wherein the transmitter equalization module is further to read, via the dedicated communication bus, requested transmitter equalization settings from the first transmitter equalization register of the first communication lane interface of the second communication device; and write, via the dedicated communication bus, the requested transmitter equalization settings of the first communication lane interface of the second communication device to the first transmitter equalization register of the first communication lane interface of the first communication device in response to the request flag being true.

Example 12 includes the subject matter of any of Examples 1-11, and wherein to read the remote transmitter equalization settings comprises to read a pre-cursor requested value from a pre-cursor request setting register bank of the first transmitter equalization register of the first communication lane interface of the second communication device, and read a post-cursor requested value from a post-cursor request setting register bank of the first transmitter equalization register of the first communication lane interface of the second communication device.

Example 13 includes the subject matter of any of Examples 1-12, and wherein the pre-cursor request setting register bank comprises bits 10 and 11 of the first transmitter equalization register of the first communication lane interface of the second communication device, and the post-cursor request setting register bank comprises bits 12, 13, and 14 of the first transmitter equalization register of the first communication lane interface of the second communication device.

Example 14 includes the subject matter of any of Examples 1-13, and wherein to write the requested transmitter equalization settings comprises to write the pre-cursor requested value to a pre-cursor local setting register bank of the first transmitter equalization register of the first communication lane interface of the first communication device; and write the post-cursor requested value to a post-cursor local setting register bank of the first transmitter equalization register of the first communication lane interface of the first communication device.

Example 15 includes the subject matter of any of Examples 1-14, and wherein the pre-cursor local setting register bank comprises bits 0 and 1 of the first transmitter equalization register of the first communication lane interface of the first communication device, and the post-cursor local setting register bank comprises bits 2, 3, and 4 of the first transmitter equalization register of the first communication lane interface of the first communication device.

Example 16 includes the subject matter of any of Examples 1-15, and wherein the transmitter equalization module is further to, after the requested transmitter equalization settings of the first communication lane interface of the second communication device have been written to the first transmitter equalization register of the first communication lane interface of the first communication device re-read, via the dedicated communication bus, the local transmitter equalization settings from the first transmitter equalization register of the first communication lane interface of the first communication device; and re-write, via the dedicated communication bus, the local transmitter equalization settings of the first communication lane interface of the first communication device to the first transmitter equalization register of the first communication lane interface of the second communication device.

Example 17 includes the subject matter of any of Examples 1-16, and wherein to re-read the local transmitter equalization settings comprises to (i) read a pre-cursor local value from a pre-cursor local setting register bank of the first transmitter equalization register of the first communication lane interface of the first communication device and (ii) read a post-cursor local value from a post-cursor local setting register bank of the first transmitter equalization register of the first communication lane interface of the first communication device, and re-write the local transmitter equalization settings comprises to (i) write the pre-cursor local value to a pre-cursor remote setting register bank of the first transmitter equalization register of the first communication lane interface of the second communication device and (ii) write the post-cursor local value to a post-cursor remote setting register bank of the first transmitter equalization register of the first communication lane interface of the second communication device.

Example 18 includes the subject matter of any of Examples 1-17, and wherein the transmitter equalization module is, in response to the request flag being false, further to read, via the dedicated communication bus, local transmitter equalization settings from a second transmitter equalization register of the first communication lane interface of the second communication device; and write, via the dedicated communication bus, the local transmitter equalization settings of the first communication lane interface of the second communication device to a second transmitter equalization register of the first communication lane interface of the first communication device, wherein the second transmitter equalization register of the first communication lane interface of the second communication device is of a communication direction different from the first transmitter equalization register of the first communication lane interface of the second communication device, and wherein the second transmitter equalization register of the first communication lane interface of the first communication device is of a communication direction different from the first transmitter equalization register of the first communication lane interface of the first communication device.

Example 19 includes the subject matter of any of Examples 1-18, and wherein to read the local transmitter equalization settings from the second transmitter equalization register of the first communication lane interface of the second communication device comprises to read a pre-cursor local value from a pre-cursor local setting register bank of the second transmitter equalization register of the first communication lane interface of the second communication device, and read a post-cursor local value from a post-cursor local setting register bank of the second transmitter equalization register of the first communication lane interface of the second communication device.

Example 20 includes the subject matter of any of Examples 1-19, and, wherein the pre-cursor local setting register bank comprises bits 0 and 1 of the second transmitter equalization register of the first communication lane interface of the second communication device, and the post-cursor local setting register bank comprises bits 2, 3, and 4 of the second transmitter equalization register of the first communication lane interface of the second communication device.

Example 21 includes the subject matter of any of Examples 1-20, and wherein to write the local transmitter equalization settings to the second transmitter equalization register of the first communication lane interface of the first communication device comprises to write the pre-cursor local value to a pre-cursor remote setting register bank of the second transmitter equalization register of the first communication lane interface of the first communication device; and write the post-cursor local value to a post-cursor remote setting register bank of the second transmitter equalization register of the first communication lane interface of the first communication device.

Example 22 includes the subject matter of any of Examples 1-21, and wherein the pre-cursor remote setting register bank comprises bits 5 and 6 of the second transmitter equalization register of the first communication lane interface of the first communication device, and the post-cursor remote setting register bank comprises bits 7, 8, and 9 of the second transmitter equalization register of the first communication lane interface of the first communication device.

Example 23 includes the subject matter of any of Examples 1-22, and wherein the transmitter equalization module is further to read, via the dedicated communication bus, a request flag from the second transmitter equalization register of the first communication lane interface of the first communication device.

Example 24 includes the subject matter of any of Examples 1-23, and wherein the request flag from the second transmitter equalization register of the first communication lane interface of the first communication device comprises bit 15 of the second transmitter equalization register of the first communication lane interface of the first communication device.

Example 25 includes the subject matter of any of Examples 1-24, and wherein the transmitter equalization module is further to read, via the dedicated communication bus, requested transmitter equalization settings from the second transmitter equalization register of the first communication lane interface of the first communication device; and write, via the dedicated communication bus, the requested transmitter equalization settings of the first communication lane interface of the first communication device to the second transmitter equalization register of the first communication lane interface of the second communication device in response to the request flag being true.

Example 26 includes the subject matter of any of Examples 1-25, and wherein to read the remote transmitter equalization settings comprises to read a pre-cursor requested value from a pre-cursor request setting register bank of the second transmitter equalization register of the first communication lane interface of the first communication device, and read a post-cursor requested value from a post-cursor request setting register bank of the second transmitter equalization register of the first communication lane interface of the first communication device.

Example 27 includes the subject matter of any of Examples 1-26, and wherein the pre-cursor request setting register bank comprises bits 10 and 11 of the second transmitter equalization register of the first communication lane interface of the first communication device, and the pre-cursor request setting register bank comprises bits 12, 13, and 14 of the second transmitter equalization register of the first communication lane interface of the first communication device.

Example 28 includes the subject matter of any of Examples 1-27, and wherein to write the requested transmitter equalization settings comprises to write the pre-cursor requested value to a pre-cursor local setting register bank of the second transmitter equalization register of the first communication lane interface of the second communication device; and write the post-cursor requested value to a post-cursor local setting register bank of the second transmitter equalization register of the first communication lane interface of the second communication device.

Example 29 includes the subject matter of any of Examples 1-28, and wherein the pre-cursor local setting register bank comprises bits 0 and 1 of the second transmitter equalization register of the first communication lane interface of the second communication device, and the post-cursor local setting register bank comprises bits 2, 3, and 4 of the second transmitter equalization register of the first communication lane interface of the second communication device.

Example 30 includes the subject matter of any of Examples 1-29, and wherein the transmitter equalization module is further to, after the requested transmitter equalization settings of the first communication lane interface of the first communication device have been written to the second transmitter equalization register of the first communication lane interface of the second communication device re-read, via the dedicated communication bus, the local transmitter equalization settings from the second transmitter equalization register of the first communication lane interface of the second communication device; and re-write, via the dedicated communication bus, the local transmitter equalization settings of the first communication lane interface of the first communication device to the second transmitter equalization register of the first communication lane interface of the first communication device.

Example 31 includes the subject matter of any of Examples 1-30, and wherein to re-read the local transmitter equalization settings comprises to (i) read a pre-cursor local value from a pre-cursor local setting register bank of the second transmitter equalization register of the first communication lane interface of the second communication device and (ii) read a post-cursor local value from a post-cursor local setting register bank of the second transmitter equalization register of the first communication lane interface of the second communication device, and re-write the local transmitter equalization settings comprises to (i) write the pre-cursor local value to a pre-cursor remote setting register bank of the second transmitter equalization register of the first communication lane interface of the first communication device and (ii) write the post-cursor local value to a post-cursor remote setting register bank of the second transmitter equalization register of the first communication lane interface of the first communication device.

Example 32 includes the subject matter of any of Examples 1-31, and wherein the second transmitter equalization register of the first communication lane interface of the first communication device has an address of 1.180, 1.181, 1.182, 1.183, 1.184, 1.185, 1.186, or 1.187.

Example 33 includes the subject matter of any of Examples 1-32, and wherein the second transmitter equalization register of the first communication lane interface of the second communication device has an address of 1.180, 1.181, 1.182, 1.183, 1.184, 1.185, 1.186, or 1.187.

Example 34 includes a station management entity of a communication controller of a communication system for performing transmitter equalization, the station management entity comprising a transmitter equalization module to read, via a management data input/output (MDIO) bus established between the station management entity and a plurality of communication devices of the communication system, a pre-cursor local value from a pre-cursor local setting register bank of a first transmitter equalization register of a first communication lane interface of a first communication device; read, via the MDIO bus, a post-cursor local value from a post-cursor local setting register bank of the first transmitter equalization register of the first communication lane interface of the first communication device; write, via the MDIO bus, the pre-cursor local value to a pre-cursor remote setting register bank of a first transmitter equalization register of a first communication lane interface of a second communication device; write, via the MDIO bus, the post-cursor local value to a post-cursor remote setting register bank of the first transmitter equalization register of the first communication lane interface of the second communication device; read, via the MDIO bus, a pre-cursor requested value from a pre-cursor request setting register bank of the first transmitter equalization register of the first communication lane interface of the second communication device; read, via the MDIO bus, a post-cursor requested value from a post-cursor request setting register bank of the first transmitter equalization register of the first communication lane interface of the second communication device; read, via the MDIO bus, a request flag from the first transmitter equalization register of the first communication lane interface of the second communication device; write, via the MDIO bus, the pre-cursor requested value to the pre-cursor local setting register bank of the first transmitter equalization register of the first communication lane interface of the first communication device in response to the request flag being true; and write, via the MDIO bus, the post-cursor requested value to the post-cursor local setting register bank of the first transmitter equalization register of the first communication lane interface of the first communication device in response to the request flag being true.

Example 35 includes the subject matter of Example 34, and wherein the pre-cursor local setting register bank of the first transmitter equalization register of the first communication lane interface of the first communication device comprises bits 0 and 1 of the first transmitter equalization register of the first communication lane interface of the first communication device, the post-cursor local setting register bank of the first transmitter equalization register of the first communication lane interface of the first communication device comprises bits 2, 3, and 4 of the first transmitter equalization register of the first communication lane interface of the first communication device, the pre-cursor remote setting register bank of the first transmitter equalization register of the first communication lane interface of the second communication device comprises bits 5 and 6 of the first transmitter equalization register of the first communication lane interface of the second communication device, the post-cursor remote setting register bank of the first transmitter equalization register of the first communication lane interface of the second communication device comprises bits 7, 8, and 9 of the first transmitter equalization register of the first communication lane interface of the second communication device, the request flag of the first transmitter equalization register of the first communication lane interface of the second communication device comprises bit 15 of the first transmitter equalization register of the first communication lane interface of the second communication device, the pre-cursor request setting register bank of the first transmitter equalization register of the first communication lane interface of the second communication device comprises bits 10 and 11 of the first transmitter equalization register of the first communication lane interface of the second communication device, the post-cursor request setting register bank of the transmitter equalization register of the first communication lane interface of the second communication device comprises bits 12, 13, and 14 of the first transmitter equalization register of the first communication lane interface of the second communication device.

Example 36 includes the subject matter of any of Examples 34 and 35, and wherein the transmitter equalization module is, in response to the request flag being false, further to read, via the MDIO bus, a pre-cursor local value from a pre-cursor local setting register bank of a second transmitter equalization register of the first communication lane interface of the second communication device; read, via the MDIO bus, a post-cursor local value from a post-cursor local setting register bank of the second transmitter equalization register of the first communication lane interface of the second communication device; write, via the MDIO bus, the pre-cursor local value read from the second transmitter equalization register of the first communication lane interface of the second communication device to a pre-cursor remote setting register bank of a second transmitter equalization register of the first communication lane interface of the first communication device; write, via the MDIO bus, the post-cursor local value read from the second transmitter equalization register of the first communication lane interface of the second communication device to a post-cursor remote setting register bank of the second transmitter equalization register of the first communication lane interface of the first communication device; read, via the MDIO bus, a pre-cursor requested value from a pre-cursor request setting register bank of the second transmitter equalization register of the first communication lane interface of the first communication device; read, via the MDIO bus, a post-cursor requested value from a post-cursor request setting register bank of the second transmitter equalization register of the first communication lane interface of the first communication device; read, via the MDIO bus, a request flag from the second transmitter equalization register of the first communication lane interface of the first communication device; write, via the MDIO bus, the pre-cursor requested value read from the second transmitter equalization register of the first communication lane interface of the first communication device to the pre-cursor local setting register bank of the second transmitter equalization register of the first communication lane interface of the second communication device in response to the request flag read from the second transmitter equalization register of the first communication lane interface of the first communication device being true; and write, via the MDIO bus, the post-cursor requested value read from the second transmitter equalization register of the first communication lane interface of the first communication device to the post-cursor local setting register bank of the second transmitter equalization register of the first communication lane interface of the second communication device in response to the request flag read from the second transmitter equalization register of the first communication lane interface of the first communication device being true.

Example 37 includes the subject matter of any of Examples 34-36, and wherein the pre-cursor local setting register bank of the second transmitter equalization register of the first communication lane interface of the second communication device comprises bits 0 and 1 of the second transmitter equalization register of the first communication lane interface of the second communication device, the post-cursor local setting register bank of the second transmitter equalization register of the first communication lane interface of the second communication device comprises bits 2, 3, and 4 of the second transmitter equalization register of the first communication lane interface of the second communication device, the pre-cursor remote setting register bank of the second transmitter equalization register of the first communication lane interface of the first communication device comprises bits 5 and 6 of the second transmitter equalization register of the first communication lane interface of the first communication device, the post-cursor remote setting register bank of the second transmitter equalization register of the first communication lane interface of the first communication device comprises bits 7, 8, and 9 of the second transmitter equalization register of the first communication lane interface of the first communication device, the request flag of the second transmitter equalization register of the first communication lane interface of the first communication device comprises bit 15 of the second transmitter equalization register of the first communication lane interface of the first communication device, the pre-cursor request setting register bank of the second transmitter equalization register of the first communication lane interface of the first communication device comprises bits 10 and 11 of the second transmitter equalization register of the first communication lane interface of the first communication device, and the post-cursor request setting register bank of the second transmitter equalization register of the first communication lane interface of the first communication device comprises bits 12, 13, and 14 of the second transmitter equalization register of the first communication lane interface of the first communication device.

Example 38 includes a first communication device for communicating with a second communication device, the first communication device comprising a chip-to-chip interface comprising a first communication lane interface to communicate with a first communication lane interface of a second communication device over a chip-to-chip communication link, the first communication lane interface comprising a transmitter, a receiver, and a transmitter equalization register; and a request module to request transmitter equalization of the first communication lane interface, wherein the request module is to set a request flag of the transmitter equalization register to request the transmitter equalization.

Example 39 includes the subject matter of Example 38, and wherein the request flag comprise bit 15 of the transmitter equalization register.

Example 40 includes the subject matter of any of Examples 38 and 39, and wherein the transmitter equalization register comprises a pre-cursor local register bank, a post-cursor local register bank, a pre-cursor remote register bank, a post-cursor remote register bank, a pre-cursor request register bank, a post-cursor request register bank, and the request flag.

Example 41 includes the subject matter of any of Examples 38-40, and wherein the pre-cursor local register bank comprises bits 0 and 1 of the transmitter equalization register; the post-cursor local register bank comprises bits 2, 3, and 4 of the transmitter equalization register; the pre-cursor remote register bank comprises bits 5 and 6 of the transmitter equalization register; the post-cursor remote register bank comprises bits 7, 8, and 9 of the transmitter equalization register; the pre-cursor request register bank comprises bits 10 and 11 of the transmitter equalization register; the post-cursor request register bank comprises bits 12, 13, and 14 of the transmitter equalization register; and the request flag comprises bit 15 of the transmitter equalization register.

Example 42 includes the subject matter of any of Examples 38-41, and wherein the request module is further to load requested transmitter equalization settings into the transmitter equalization register.

Example 43 includes the subject matter of any of Examples 38-42, and wherein to load the requested transmitter equalization settings comprises to set a pre-cursor requested register bank of the transmitter equalization register to a first desired value and set a post-cursor requested register bank of the transmitter equalization register to a second desired value.

Example 44 includes the subject matter of any of Examples 38-43, and wherein the pre-cursor requested register bank comprises bits 10 and 11 of the transmitter equalization register and the post-cursor requested register bank comprises bits 12, 13, and 14 of the transmitter equalization register.

Example 45 includes the subject matter of any of Examples 38-44, and wherein the chip-to-chip interface further comprises a second communication lane interface to communicate with a second communication lane interface of the second communication device over the chip-to-chip communication link; a third communication lane interface to communicate with a third communication lane interface of the second communication device over the chip-to-chip communication link; and a fourth communication lane interface to communicate with a fourth communication lane interface of the second communication device over the chip-to-chip communication link, wherein each of the second, third, and fourth communication lane interfaces include a separate transmitter, receiver, and transmitter equalization register.

Example 46 includes a method for performing transmitter equalization in a communication system, the method comprising reading, by a station management entity and over a dedicated communication bus established between the station management entity and a plurality of communication devices of the communication system, local transmitter equalization settings from a first transmitter equalization register of a first communication lane interface of a first communication device; and writing, by the station management entity and over the dedicated communication bus, the local transmitter equalization settings of the first communication lane interface of the first communication device to a first transmitter equalization register of a first communication lane interface of a second communication device, wherein the first communication lane interface of the first communication device is communicatively coupled with the first communication lane interface of the second communication device via a chip-to-chip communication link different from the dedicated communication bus.

Example 47 includes the subject matter of Example 46, and wherein reading the local transmitter equalization settings comprises reading, over a management data input/output (MDIO) bus, the local transmitter equalization settings, and writing the local transmitter equalization settings comprises writing, over the MDIO bus, the local transmitter equalization settings.

Example 48 includes the subject matter of any of Examples 46 and 47, and wherein reading the local transmitter equalization settings comprises reading a pre-cursor local value from a pre-cursor local setting register bank of the first transmitter equalization register of the first communication lane interface of the first communication device, and reading a post-cursor local value from a post-cursor local setting register bank of the first transmitter equalization register of the first communication lane interface of the first communication device.

Example 49 includes the subject matter of any of Examples 46-48, and wherein reading the pre-cursor local value comprises reading bits 0 and 1 of first transmitter equalization register of the first communication lane interface of the first communication device, and reading the post-cursor local value comprises reading bits 2, 3, and 4 of the first transmitter equalization register of the first communication lane interface of the first communication device.

Example 50 includes the subject matter of any of Examples 46-49, and wherein writing the local transmitter equalization settings comprises writing the pre-cursor local value to a pre-cursor remote setting register bank of the first transmitter equalization register of the first communication lane interface of the second communication device; and writing the post-cursor local value to a post-cursor remote setting register bank of the first transmitter equalization register of the first communication lane interface of the second communication device.

Example 51 includes the subject matter of any of Examples 46-50, and wherein writing the pre-cursor local value comprises writing to bits 5 and 6 of the first transmitter equalization register of the first communication lane interface of the second communication device, and writing the post-cursor local value comprises writing to bits 7, 8, and 9 of the first transmitter equalization register of the first communication lane interface of the second communication device.

Example 52 includes the subject matter of any of Examples 46-51, and wherein reading the local transmitter equalization settings from the first transmitter equalization register of the first communication lane interface of the first communication device comprises reading a register located at the address of 1.180, 1.181, 1.182, 1.183, 1.184, 1.185, 1.186, or 1.87.

Example 53 includes the subject matter of any of Examples 46-52, and wherein writing the local transmitter equalization settings to the first transmitter equalization register of the first communication lane interface of the second communication device comprises writing to a register located at the address of 1.180, 1.181, 1.182, 1.183, 1.184, 1.185, 1.186, or 1.87.

Example 54 includes the subject matter of any of Examples 46-53, and further including reading, by the station management entity and over the dedicated communication bus, a request flag from the first transmitter equalization register of the first communication lane interface of the second communication device.

Example 55 includes the subject matter of any of Examples 46-54, and wherein reading the request flag from the first transmitter equalization register comprises reading bit 15 of the first transmitter equalization register of the first communication lane interface of the second communication device.

Example 56 includes the subject matter of any of Examples 46-55, and further including reading, by a station management entity and over the dedicated communication bus, requested transmitter equalization settings from the first transmitter equalization register of the first communication lane interface of the second communication device; and writing, by the station management entity and over the dedicated communication bus, the requested transmitter equalization settings of the first communication lane interface of the second communication device to the first transmitter equalization register of the first communication lane interface of the first communication device in response to the request flag being true.

Example 57 includes the subject matter of any of Examples 46-56, and wherein reading the remote transmitter equalization settings comprises reading a pre-cursor requested value from a pre-cursor request setting register bank of the first transmitter equalization register of the first communication lane interface of the second communication device, and reading a post-cursor requested value from a post-cursor request setting register bank of the first transmitter equalization register of the first communication lane interface of the second communication device.

Example 58 includes the subject matter of any of Examples 46-57, and wherein reading the pre-cursor requested value comprises reading bits 10 and 11 of the first transmitter equalization register of the first communication lane interface of the second communication device, and reading the post-cursor requested value comprises reading bits 12, 13, and 14 of the first transmitter equalization register of the first communication lane interface of the second communication device.

Example 59 includes the subject matter of any of Examples 46-58, and wherein writing the requested transmitter equalization settings comprises writing the pre-cursor requested value to a pre-cursor local setting register bank of the first transmitter equalization register of the first communication lane interface of the first communication device; and writing the post-cursor requested value to a post-cursor local setting register bank of the first transmitter equalization register of the first communication lane interface of the first communication device.

Example 60 includes the subject matter of any of Examples 46-59, and wherein writing the pre-cursor requested value comprises writing to bits 0 and 1 of the first transmitter equalization register of the first communication lane interface of the first communication device, and writing the post-cursor requested value comprises writing to bits 2, 3, and 4 of the first transmitter equalization register of the first communication lane interface of the first communication device.

Example 61 includes the subject matter of any of Examples 46-60, and further including, subsequently to the writing of the requested transmitter equalization settings of the first communication lane interface of the second communication device to the first transmitter equalization register of the first communication lane interface of the first communication device, re-reading, by the station management entity and over the dedicated communication bus, the local transmitter equalization settings from the first transmitter equalization register of the first communication lane interface of the first communication device; and re-writing, by the station management entity and over the dedicated communication bus, the local transmitter equalization settings of the first communication lane interface of the first communication device to the first transmitter equalization register of the first communication lane interface of the second communication device.

Example 62 includes the subject matter of any of Examples 46-61, and wherein re-reading the local transmitter equalization settings comprises (i) reading a pre-cursor local value from a pre-cursor local setting register bank of the first transmitter equalization register of the first communication lane interface of the first communication device and (ii) reading a post-cursor local value from a post-cursor local setting register bank of the first transmitter equalization register of the first communication lane interface of the first communication device, and re-writing the local transmitter equalization settings comprises (i) writing the pre-cursor local value to a pre-cursor remote setting register bank of the first transmitter equalization register of the first communication lane interface of the second communication device and (ii) writing the post-cursor local value to a post-cursor remote setting register bank of the first transmitter equalization register of the first communication lane interface of the second communication device.

Example 63 includes the subject matter of any of Examples 46-62, and further including, in response to the request flag being false, reading, by the station management entity and over the dedicated communication bus, local transmitter equalization settings from a second transmitter equalization register of the first communication lane interface of the second communication device; and writing, by the station management entity and over the dedicated communication bus, the local transmitter equalization settings of the first communication lane interface of the second communication device to a second transmitter equalization register of the first communication lane interface of the first communication device, wherein the second transmitter equalization register of the first communication lane interface of the second communication device is of a communication direction different from the first transmitter equalization register of the first communication lane interface of the second communication device, and wherein the second transmitter equalization register of the first communication lane interface of the first communication device is of a communication direction different from the first transmitter equalization register of the first communication lane interface of the first communication device.

Example 64 includes the subject matter of any of Examples 46-63, and wherein reading the local transmitter equalization settings from the second transmitter equalization register of the first communication lane interface of the second communication device comprises reading a pre-cursor local value from a pre-cursor local setting register bank of the second transmitter equalization register of the first communication lane interface of the second communication device, and reading a post-cursor local value from a post-cursor local setting register bank of the second transmitter equalization register of the first communication lane interface of the second communication device.

Example 65 includes the subject matter of any of Examples 46-64, and wherein reading the pre-cursor local value comprises reading bits 0 and 1 of the second transmitter equalization register of the first communication lane interface of the second communication device, and reading the post-cursor local value comprises reading bits 2, 3, and 4 of the second transmitter equalization register of the first communication lane interface of the second communication device.

Example 66 includes the subject matter of any of Examples 46-65, and wherein writing the local transmitter equalization settings to the second transmitter equalization register of the first communication lane interface of the first communication device comprises writing the pre-cursor local value to a pre-cursor remote setting register bank of the second transmitter equalization register of the first communication lane interface of the first communication device; and writing the post-cursor local value to a post-cursor remote setting register bank of the second transmitter equalization register of the first communication lane interface of the first communication device.

Example 67 includes the subject matter of any of Examples 46-66, and wherein writing the pre-cursor local value comprises writing to bits 5 and 6 of the second transmitter equalization register of the first communication lane interface of the first communication device, and writing the post-cursor local value comprises writing to bits 7, 8, and 9 of the second transmitter equalization register of the first communication lane interface of the first communication device.

Example 68 includes the subject matter of any of Examples 46-67, and further including reading, by the station management entity and over the dedicated communication bus, a request flag from the second transmitter equalization register of the first communication lane interface of the first communication device.

Example 69 includes the subject matter of any of Examples 46-68, and wherein reading the request flag from the second transmitter equalization register of the first communication lane interface of the first communication device comprises reading bit 15 of the second transmitter equalization register of the first communication lane interface of the first communication device.

Example 70 includes the subject matter of any of Examples 46-69, and further including reading, by a station management entity and over the dedicated communication bus, requested transmitter equalization settings from the second transmitter equalization register of the first communication lane interface of the first communication device; and writing, by the station management entity and over the dedicated communication bus, the requested transmitter equalization settings of the first communication lane interface of the first communication device to the second transmitter equalization register of the first communication lane interface of the second communication device in response to the request flag being true.

Example 71 includes the subject matter of any of Examples 46-70, and wherein reading the remote transmitter equalization settings comprises reading a pre-cursor requested value from a pre-cursor request setting register bank of the second transmitter equalization register of the first communication lane interface of the first communication device, and reading a post-cursor requested value from a post-cursor request setting register bank of the second transmitter equalization register of the first communication lane interface of the first communication device.

Example 72 includes the subject matter of any of Examples 46-71, and wherein reading the pre-cursor requested value comprises reading bits 10 and 11 of the second transmitter equalization register of the first communication lane interface of the first communication device, and reading the post-cursor requested value comprises reading bits 12, 13, and 14 of the second transmitter equalization register of the first communication lane interface of the first communication device.

Example 73 includes the subject matter of any of Examples 46-72, and wherein writing the requested transmitter equalization settings comprises writing the pre-cursor requested value to a pre-cursor local setting register bank of the second transmitter equalization register of the first communication lane interface of the second communication device; and writing the post-cursor requested value to a post-cursor local setting register bank of the second transmitter equalization register of the first communication lane interface of the second communication device.

Example 74 includes the subject matter of any of Examples 46-73, and wherein writing the pre-cursor requested value comprises writing to bits 0 and 1 of the second transmitter equalization register of the first communication lane interface of the second communication device, and writing the post-cursor requested value comprises writing to bits 2, 3, and 4 of the second transmitter equalization register of the first communication lane interface of the second communication device.

Example 75 includes the subject matter of any of Examples 46-74, and further including, subsequently to the writing of the requested transmitter equalization settings of the first communication lane interface of the first communication device to the second transmitter equalization register of the first communication lane interface of the second communication device, re-reading, by the station management entity and over the dedicated communication bus, the local transmitter equalization settings from the second transmitter equalization register of the first communication lane interface of the second communication device; and re-writing, by the station management entity and over the dedicated communication bus, the local transmitter equalization settings of the first communication lane interface of the first communication device to the second transmitter equalization register of the first communication lane interface of the first communication device.

Example 76 includes the subject matter of any of Examples 46-75, and wherein re-reading the local transmitter equalization settings comprises (i) reading a pre-cursor local value from a pre-cursor local setting register bank of the second transmitter equalization register of the first communication lane interface of the second communication device and (ii) reading a post-cursor local value from a post-cursor local setting register bank of the second transmitter equalization register of the first communication lane interface of the second communication device, and re-writing the local transmitter equalization settings comprises (i) writing the pre-cursor local value to a pre-cursor remote setting register bank of the second transmitter equalization register of the first communication lane interface of the first communication device and (ii) writing the post-cursor local value to a post-cursor remote setting register bank of the second transmitter equalization register of the first communication lane interface of the first communication device.

Example 77 includes the subject matter of any of Examples 46-76, and wherein reading the local transmitter equalization settings from the second transmitter equalization register of the first communication lane interface of the first communication device comprises reading a register of the first communication lane interface of the first communication device located at the address of 1.180, 1.181, 1.182, 1.183, 1.184, 1.185, 1.186, or 1.187.

Example 78 includes the subject matter of any of Examples 46-77, and wherein writing the local transmitter equalization settings to the second transmitter equalization register of the first communication lane interface of the second communication device comprises writing to a register of the first communication lane interface of the second communication device located at the address of 1.180, 1.181, 1.182, 1.183, 1.184, 1.185, 1.186, or 1.187.

Example 79 includes a method for performing transmitter equalization in a communication system, the method comprising reading, by a station management entity and over a management data input/output (MDIO) bus established between the station management entity and a plurality of communication devices of the communication system, a pre-cursor local value from a pre-cursor local setting register bank of a first transmitter equalization register of a first communication lane interface of a first communication device; reading, by the station management entity and over the MDIO bus, a post-cursor local value from a post-cursor local setting register bank of the first transmitter equalization register of the first communication lane interface of the first communication device; writing, by the station management entity and over the MDIO bus, the pre-cursor local value to a pre-cursor remote setting register bank of a first transmitter equalization register of a first communication lane interface of a second communication device; writing, by the station management entity and over the MDIO bus, the post-cursor local value to a post-cursor remote setting register bank of the first transmitter equalization register of the first communication lane interface of the second communication device; reading, by the station management entity and over the MDIO bus, a pre-cursor requested value from a pre-cursor request setting register bank of the first transmitter equalization register of the first communication lane interface of the second communication device; reading, by the station management entity and over the MDIO bus, a post-cursor requested value from a post-cursor request setting register bank of the first transmitter equalization register of the first communication lane interface of the second communication device; reading, by the station management entity and over the MDIO bus, a request flag from the first transmitter equalization register of the first communication lane interface of the second communication device; writing, by the station management entity and over the MDIO bus, the pre-cursor requested value to the pre-cursor local setting register bank of the first transmitter equalization register of the first communication lane interface of the first communication device in response to the request flag being true; and writing, by the station management entity and over the MDIO bus, the post-cursor requested value to the post-cursor local setting register bank of the first transmitter equalization register of the first communication lane interface of the first communication device in response to the request flag being true, wherein the first communication lane interface of the first communication device is communicatively coupled with the first communication lane interface of the second communication device via a chip-to-chip communication link different from the dedicated communication bus.

Example 80 includes the subject matter of Example 79, and wherein reading the pre-cursor local value comprises reading bits 0 and 1 of the first transmitter equalization register of the first communication lane interface of the first communication device, reading the post-cursor local value comprises reading bits 2, 3, and 4 of the first transmitter equalization register of the first communication lane interface of the first communication device, writing the pre-cursor local value comprises writing to bits 5 and 6 of the first transmitter equalization register of the first communication lane interface of the second communication device, writing the post-cursor local value comprises writing to bits 7, 8, and 9 of the first transmitter equalization register of the first communication lane interface of the second communication device, reading the request flag from the transmitter equalization register comprises reading bit 15 of the first transmitter equalization register of the first communication lane interface of the second communication device, reading the pre-cursor requested value comprises reading bits 10 and 11 of the first transmitter equalization register of the first communication lane interface of the second communication device, reading the post-cursor requested value comprises reading bits 12, 13, and 14 of the first equalization register of the first communication lane interface of the second communication device, writing the pre-cursor requested value comprises writing to bits 0 and 1 of the first transmitter equalization register of the first communication lane interface of the first communication device, and writing the post-cursor requested value comprises writing to bits 2, 3, and 4 of the first transmitter equalization register of the first communication lane interface of the first communication device.

Example 81 includes the subject matter of any of Examples 79 and 80, and further including, in response to the request flag being false, reading, by the station management entity and over the MDIO bus, a pre-cursor local value from a pre-cursor local setting register bank of a second transmitter equalization register of the first communication lane interface of the second communication device; reading, by the station management entity and over the MDIO bus, a post-cursor local value from a post-cursor local setting register bank of the second transmitter equalization register of the first communication lane interface of the second communication device; writing, by the station management entity and over the MDIO bus, the pre-cursor local value read from the second transmitter equalization register of the first communication lane interface of the second communication device to a pre-cursor remote setting register bank of a second transmitter equalization register of the first communication lane interface of the first communication device; writing, by the station management entity and over the MDIO bus, the post-cursor local value read from the second transmitter equalization register of the first communication lane interface of the second communication device to a post-cursor remote setting register bank of the second transmitter equalization register of the first communication lane interface of the first communication device; reading, by the station management entity and over the MDIO bus, a pre-cursor requested value from a pre-cursor request setting register bank of the second transmitter equalization register of the first communication lane interface of the first communication device; reading, by the station management entity and over the MDIO bus, a post-cursor requested value from a post-cursor request setting register bank of the second transmitter equalization register of the first communication lane interface of the first communication device; reading, by the station management entity and over the MDIO bus, a request flag from the second transmitter equalization register of the first communication lane interface of the first communication device; writing, by the station management entity and over the MDIO bus, the pre-cursor requested value read from the second transmitter equalization register of the first communication lane interface of the first communication device to the pre-cursor local setting register bank of the second transmitter equalization register of the first communication lane interface of the second communication device in response to the request flag read from the second transmitter equalization register of the first communication lane interface of the first communication device being true; and writing, by the station management entity and over the MDIO bus, the post-cursor requested value read from the second transmitter equalization register of the first communication lane interface of the first communication device to a post-cursor local setting register bank of the second transmitter equalization register of the first communication lane interface of the second communication device in response to the request flag read from the second transmitter equalization register of the first communication lane interface of the first communication device being true.

Example 82 includes the subject matter of any of Examples 79-81, and wherein reading the pre-cursor local value from the second transmitter equalization register of the first communication lane interface of the second communication device comprises reading bits 0 and 1 of the second transmitter equalization register of the first communication lane interface of the second communication device, reading the post-cursor local value from the second transmitter equalization register of the first communication lane interface of the second communication device comprises reading bits 2, 3, and 4 of the second transmitter equalization register of the first communication lane interface of the second communication device, writing the pre-cursor local value to the pre-cursor remote setting register bank of the second transmitter equalization register of the first communication lane interface of the first communication device comprises writing to bits 5 and 6 of the second transmitter equalization register of the first communication lane interface of the first communication device, writing the post-cursor local value to the post-cursor remote setting register bank of the second transmitter equalization register of the first communication lane interface of the first communication device comprises writing to bits 7, 8, and 9 of the second transmitter equalization register of the first communication lane interface of the first communication device, reading the request flag from the second transmitter equalization register of the first communication lane interface of the first communication device comprises reading bit 15 of the second transmitter equalization register of the first communication lane interface of the first communication device, reading the pre-cursor requested value from the second transmitter equalization register of the first communication lane interface of the first communication device comprises reading bits 10 and 11 of the second transmitter equalization register of the first communication lane interface of the first communication device, and reading the post-cursor requested value from the second transmitter equalization register of the first communication lane interface of the first communication device comprises reading bits 12, 13, and 14 of the second transmitter equalization register of the first communication lane interface of the first communication device, writing the pre-cursor requested value to the pre-cursor local setting register bank of the second transmitter equalization register of the first communication lane interface of the second communication device comprises writing to bits 0 and 1 of the second transmitter equalization register of the first communication lane interface of the second communication device, and writing the post-cursor requested value to the post-cursor local setting register bank of the second transmitter equalization register of the first communication lane interface of the second communication device comprises writing to bits 2, 3, and 4 of the second transmitter equalization register of the first communication lane interface of the second communication device.

Example 83 includes a method for requesting transmitter equalization in a first communication device, the method comprising loading requested transmitter equalization settings into a transmitter equalization register of a first communication lane interface of the first communication device, wherein the first communication lane interface of the first communication device is communicatively coupled with a first communication lane interface of a second communication device via a chip-to-chip communication link, and setting a request flag of a transmitter equalization register of the first communication lane interface of the first communication device.

Example 84 includes the subject matter of Example 83, and wherein setting the request flag comprises setting bit 15 of the transmitter equalization register.

Example 85 includes the subject matter of any of Examples 83 and 84, and wherein loading the requested transmitter equalization settings comprises setting a pre-cursor requested register bank of the transmitter equalization register to a first desired value and setting a post-cursor requested register bank of the transmitter equalization register to a second desired value.

Example 86 includes the subject matter of any of Examples 83-85, and wherein setting the pre-cursor requested register bank comprises setting bits 10 and 11 of the transmitter equalization register, and setting the post-cursor requested register bank comprises setting bits 12, 13, and 14 of the transmitter equalization register.

Example 87 includes the subject matter of any of Examples 83-86, and wherein the transmitter equalization register comprises a pre-cursor local register bank, a post-cursor local register bank, a pre-cursor remote register bank, a post-cursor remote register bank, a pre-cursor request register bank, a post-cursor request register bank, and the request flag.

Example 88 includes the subject matter of any of Examples 83-87, and wherein the pre-cursor local register bank comprises bits 0 and 1 of the transmitter equalization register; the post-cursor local register bank comprises bits 2, 3, and 4 of the transmitter equalization register; the pre-cursor remote register bank comprises bits 5 and 6 of the transmitter equalization register; the post-cursor remote register bank comprises bits 7, 8, and 9 of the transmitter equalization register; the pre-cursor request register bank comprises bits 10 and 11 of the transmitter equalization register; the post-cursor request register bank comprises bits 12, 13, and 14 of the transmitter equalization register; and the request flag comprises bit 15 of the transmitter equalization register.

Example 89 includes one or more machine readable storage media comprising a plurality of instructions stored thereon that in response to being executed result in a communication device performing the method of any of Examples 46-88.

Example 90 includes a station management entity to read, over a management data input/output (MDIO) bus established between the station management entity and a plurality of communication devices, a pre-cursor local value from a pre-cursor local setting register bank of a first transmitter equalization register of a first communication lane interface of a first communication device; read, over the MDIO bus, a post-cursor local value from a post-cursor local setting register bank of the first transmitter equalization register of the first communication lane interface of the first communication device; write, over the MDIO bus, the pre-cursor local value to a pre-cursor remote setting register bank of a first transmitter equalization register of a first communication lane interface of a second communication device; write, over the MDIO bus, the post-cursor local value to a post-cursor remote setting register bank of the first transmitter equalization register of the first communication lane interface of the second communication device; read, over the MDIO bus, a pre-cursor requested value from a pre-cursor request setting register bank of the first transmitter equalization register of the first communication lane interface of the second communication device; read, and over the MDIO bus, a post-cursor requested value from a post-cursor request setting register bank of the first transmitter equalization register of the first communication lane interface of the second communication device; read, over the MDIO bus, a request flag from the first transmitter equalization register of the first communication lane interface of the second communication device; write, over the MDIO bus, the pre-cursor requested value to the pre-cursor local setting register bank of the first transmitter equalization register of the first communication lane interface of the first communication device in response to the request flag being true; and write, over the MDIO bus, the post-cursor requested value to the post-cursor local setting register bank of the first transmitter equalization register of the first communication lane interface of the first communication device in response to the request flag being true.

Example 91 includes the subject matter of Example 90, and wherein to read the pre-cursor local value comprises reading bits 0 and 1 of the first transmitter equalization register of the first communication lane interface of the first communication device, to read the post-cursor local value comprises reading bits 2, 3, and 4 of the first transmitter equalization register of the first communication lane interface of the first communication device, to write the pre-cursor local value comprises writing to bits 5 and 6 of the first transmitter equalization register of the first communication lane interface of the second communication device, to write the post-cursor local value comprises writing to bits 7, 8, and 9 of the first transmitter equalization register of the first communication lane interface of the second communication device, to read the request flag from the transmitter equalization register comprises reading bit 15 of the first transmitter equalization register of the first communication lane interface of the second communication device, to read the pre-cursor requested value comprises reading bits 10 and 11 of the first transmitter equalization register of the first communication lane interface of the second communication device, to read the post-cursor requested value comprises reading bits 12, 13, and 14 of the first equalization register of the first communication lane interface of the second communication device, to write the pre-cursor requested value comprises writing to bits 0 and 1 of the first transmitter equalization register of the first communication lane interface of the first communication device, and to write the post-cursor requested value comprises writing to bits 2, 3, and 4 of the first transmitter equalization register of the first communication lane interface of the first communication device.

Example 92 includes the subject matter of any of Examples 90 and 91, and to further, in response to the request flag being false, to read, over the MDIO bus, a pre-cursor local value from a pre-cursor local setting register bank of a second transmitter equalization register of the first communication lane interface of the second communication device; to read, over the MDIO bus, a post-cursor local value from a post-cursor local setting register bank of the second transmitter equalization register of the first communication lane interface of the second communication device; to write, over the MDIO bus, the pre-cursor local value read from the second transmitter equalization register of the first communication lane interface of the second communication device to a pre-cursor remote setting register bank of a second transmitter equalization register of the first communication lane interface of the first communication device; to write, over the MDIO bus, the post-cursor local value read from the second transmitter equalization register of the first communication lane interface of the second communication device to a post-cursor remote setting register bank of the second transmitter equalization register of the first communication lane interface of the first communication device; to read, over the MDIO bus, a pre-cursor requested value from a pre-cursor request setting register bank of the second transmitter equalization register of the first communication lane interface of the first communication device; to read, over the MDIO bus, a post-cursor requested value from a post-cursor request setting register bank of the second transmitter equalization register of the first communication lane interface of the first communication device; to read, over the MDIO bus, a request flag from the second transmitter equalization register of the first communication lane interface of the first communication device; to write, over the MDIO bus, the pre-cursor requested value read from the second transmitter equalization register of the first communication lane interface of the first communication device to the pre-cursor local setting register bank of the second transmitter equalization register of the first communication lane interface of the second communication device in response to the request flag read from the second transmitter equalization register of the first communication lane interface of the first communication device being true; and to write, over the MDIO bus, the post-cursor requested value read from the second transmitter equalization register of the first communication lane interface of the first communication device to a post-cursor local setting register bank of the second transmitter equalization register of the first communication lane interface of the second communication device in response to the request flag read from the second transmitter equalization register of the first communication lane interface of the first communication device being true.

Example 93 includes the subject matter of any of Examples 90-92, and wherein to read the pre-cursor local value from the second transmitter equalization register of the first communication lane interface of the second communication device comprises reading bits 0 and 1 of the second transmitter equalization register of the first communication lane interface of the second communication device, to read the post-cursor local value from the second transmitter equalization register of the first communication lane interface of the second communication device comprises reading bits 2, 3, and 4 of the second transmitter equalization register of the first communication lane interface of the second communication device, to write the pre-cursor local value to the pre-cursor remote setting register bank of the second transmitter equalization register of the first communication lane interface of the first communication device comprises writing to bits 5 and 6 of the second transmitter equalization register of the first communication lane interface of the first communication device, to write the post-cursor local value to the post-cursor remote setting register bank of the second transmitter equalization register of the first communication lane interface of the first communication device comprises writing to bits 7, 8, and 9 of the second transmitter equalization register of the first communication lane interface of the first communication device, to read the request flag from the second transmitter equalization register of the first communication lane interface of the first communication device comprises reading bit 15 of the second transmitter equalization register of the first communication lane interface of the first communication device, to read the pre-cursor requested value from the second transmitter equalization register of the first communication lane interface of the first communication device comprises reading bits 10 and 11 of the second transmitter equalization register of the first communication lane interface of the first communication device, and to read the post-cursor requested value from the second transmitter equalization register of the first communication lane interface of the first communication device comprises reading bits 12, 13, and 14 of the second transmitter equalization register of the first communication lane interface of the first communication device, to write the pre-cursor requested value to the pre-cursor local setting register bank of the second transmitter equalization register of the first communication lane interface of the second communication device comprises writing to bits 0 and 1 of the second transmitter equalization register of the first communication lane interface of the second communication device, and to write the post-cursor requested value to the post-cursor local setting register bank of the second transmitter equalization register of the first communication lane interface of the second communication device comprises writing to bits 2, 3, and 4 of the second transmitter equalization register of the first communication lane interface of the second communication device.

Example 94 includes a first communication device to load requested transmitter equalization settings into a transmitter equalization register of a first communication lane interface of the first communication device, wherein the first communication lane interface of the first communication device is communicatively coupled with a first communication lane interface of a second communication device via a chip-to-chip communication link, and set a request flag of a transmitter equalization register of the first communication lane interface of the first communication device.

Example 95 includes the subject matter of Example 94, and wherein to set the request flag comprises setting bit 15 of the transmitter equalization register.

Example 96 includes the subject matter of any of Examples 94 and 95, and wherein to load the requested transmitter equalization settings comprises setting a pre-cursor requested register bank of the transmitter equalization register to a first desired value and to set a post-cursor requested register bank of the transmitter equalization register to a second desired value.

Example 97 includes the subject matter of any of Examples 94-96, and wherein to set the pre-cursor requested register bank comprises setting bits 10 and 11 of the transmitter equalization register, and to set the post-cursor requested register bank comprises setting bits 12, 13, and 14 of the transmitter equalization register.

Example 98 includes the subject matter of any of Examples 94-97, and wherein the transmitter equalization register comprises a pre-cursor local register bank, a post-cursor local register bank, a pre-cursor remote register bank, a post-cursor remote register bank, a pre-cursor request register bank, a post-cursor request register bank, and the request flag.

Example 99 includes the subject matter of any of Examples 94-98, and wherein the pre-cursor local register bank comprises bits 0 and 1 of the transmitter equalization register; the post-cursor local register bank comprises bits 2, 3, and 4 of the transmitter equalization register; the pre-cursor remote register bank comprises bits 5 and 6 of the transmitter equalization register; the post-cursor remote register bank comprises bits 7, 8, and 9 of the transmitter equalization register; the pre-cursor request register bank comprises bits 10 and 11 of the transmitter equalization register; the post-cursor request register bank comprises bits 12, 13, and 14 of the transmitter equalization register; and the request flag comprises bit 15 of the transmitter equalization register.

Example 100 includes one or more machine readable storage media comprising a plurality of instructions stored thereon that, in response to execution, cause a station management entity to read, over a management data input/output (MDIO) bus established between the station management entity and a plurality of communication devices of the communication system, a pre-cursor local value from a pre-cursor local setting register bank of a first transmitter equalization register of a first communication lane interface of a first communication device; read, over the MDIO bus, a post-cursor local value from a post-cursor local setting register bank of the first transmitter equalization register of the first communication lane interface of the first communication device; write, over the MDIO bus, the pre-cursor local value to a pre-cursor remote setting register bank of a first transmitter equalization register of a first communication lane interface of a second communication device; write, over the MDIO bus, the post-cursor local value to a post-cursor remote setting register bank of the first transmitter equalization register of the first communication lane interface of the second communication device; read, over the MDIO bus, a pre-cursor requested value from a pre-cursor request setting register bank of the first transmitter equalization register of the first communication lane interface of the second communication device; read, over the MDIO bus, a post-cursor requested value from a post-cursor request setting register bank of the first transmitter equalization register of the first communication lane interface of the second communication device; read, over the MDIO bus, a request flag from the first transmitter equalization register of the first communication lane interface of the second communication device; write, over the MDIO bus, the pre-cursor requested value to the pre-cursor local setting register bank of the first transmitter equalization register of the first communication lane interface of the first communication device in response to the request flag being true; and write, over the MDIO bus, the post-cursor requested value to the post-cursor local setting register bank of the first transmitter equalization register of the first communication lane interface of the first communication device in response to the request flag being true, wherein the first communication lane interface of the first communication device is communicatively coupled with the first communication lane interface of the second communication device via a chip-to-chip communication link different from the dedicated communication bus.

Example 101 includes the subject matter of Example 100, and wherein read the pre-cursor local value comprises to read bits 0 and 1 of the first transmitter equalization register of the first communication lane interface of the first communication device, to read the post-cursor local value comprises to read bits 2, 3, and 4 of the first transmitter equalization register of the first communication lane interface of the first communication device, to write the pre-cursor local value comprises to write to bits 5 and 6 of the first transmitter equalization register of the first communication lane interface of the second communication device, to write the post-cursor local value comprises to write to bits 7, 8, and 9 of the first transmitter equalization register of the first communication lane interface of the second communication device, to read the request flag from the transmitter equalization register comprises to read bit 15 of the first transmitter equalization register of the first communication lane interface of the second communication device, to read the pre-cursor requested value comprises to read bits 10 and 11 of the first transmitter equalization register of the first communication lane interface of the second communication device, to read the post-cursor requested value comprises to read bits 12, 13, and 14 of the first equalization register of the first communication lane interface of the second communication device, to write the pre-cursor requested value comprises to write to bits 0 and 1 of the first transmitter equalization register of the first communication lane interface of the first communication device, and to write the post-cursor requested value comprises to write to bits 2, 3, and 4 of the first transmitter equalization register of the first communication lane interface of the first communication device.

Example 102 includes the subject matter of any of Examples 100 and 101, and wherein the plurality of instructions further cause the station management entity, in response to the request flag being false, to read, over the MDIO bus, a pre-cursor local value from a pre-cursor local setting register bank of a second transmitter equalization register of the first communication lane interface of the second communication device; read, over the MDIO bus, a post-cursor local value from a post-cursor local setting register bank of the second transmitter equalization register of the first communication lane interface of the second communication device; write, over the MDIO bus, the pre-cursor local value read from the second transmitter equalization register of the first communication lane interface of the second communication device to a pre-cursor remote setting register bank of a second transmitter equalization register of the first communication lane interface of the first communication device; write, over the MDIO bus, the post-cursor local value read from the second transmitter equalization register of the first communication lane interface of the second communication device to a post-cursor remote setting register bank of the second transmitter equalization register of the first communication lane interface of the first communication device; read, over the MDIO bus, a pre-cursor requested value from a pre-cursor request setting register bank of the second transmitter equalization register of the first communication lane interface of the first communication device; read, over the MDIO bus, a post-cursor requested value from a post-cursor request setting register bank of the second transmitter equalization register of the first communication lane interface of the first communication device; read, over the MDIO bus, a request flag from the second transmitter equalization register of the first communication lane interface of the first communication device; write, over the MDIO bus, the pre-cursor requested value read from the second transmitter equalization register of the first communication lane interface of the first communication device to the pre-cursor local setting register bank of the second transmitter equalization register of the first communication lane interface of the second communication device in response to the request flag read from the second transmitter equalization register of the first communication lane interface of the first communication device being true; and write, over the MDIO bus, the post-cursor requested value read from the second transmitter equalization register of the first communication lane interface of the first communication device to a post-cursor local setting register bank of the second transmitter equalization register of the first communication lane interface of the second communication device in response to the request flag read from the second transmitter equalization register of the first communication lane interface of the first communication device being true.

Example 103 includes the subject matter of any of Examples 100-102, and wherein to read the pre-cursor local value from the second transmitter equalization register of the first communication lane interface of the second communication device comprises to read bits 0 and 1 of the second transmitter equalization register of the first communication lane interface of the second communication device, to read the post-cursor local value from the second transmitter equalization register of the first communication lane interface of the second communication device comprises to read bits 2, 3, and 4 of the second transmitter equalization register of the first communication lane interface of the second communication device, to write the pre-cursor local value to the pre-cursor remote setting register bank of the second transmitter equalization register of the first communication lane interface of the first communication device comprises to write to bits 5 and 6 of the second transmitter equalization register of the first communication lane interface of the first communication device, to write the post-cursor local value to the post-cursor remote setting register bank of the second transmitter equalization register of the first communication lane interface of the first communication device comprises to write to bits 7, 8, and 9 of the second transmitter equalization register of the first communication lane interface of the first communication device, to read the request flag from the second transmitter equalization register of the first communication lane interface of the first communication device comprises to read bit 15 of the second transmitter equalization register of the first communication lane interface of the first communication device, to read the pre-cursor requested value from the second transmitter equalization register of the first communication lane interface of the first communication device comprises to read bits 10 and 11 of the second transmitter equalization register of the first communication lane interface of the first communication device, and to read the post-cursor requested value from the second transmitter equalization register of the first communication lane interface of the first communication device comprises to read bits 12, 13, and 14 of the second transmitter equalization register of the first communication lane interface of the first communication device, to write the pre-cursor requested value to the pre-cursor local setting register bank of the second transmitter equalization register of the first communication lane interface of the second communication device comprises to write to bits 0 and 1 of the second transmitter equalization register of the first communication lane interface of the second communication device, and to write the post-cursor requested value to the post-cursor local setting register bank of the second transmitter equalization register of the first communication lane interface of the second communication device comprises to write to bits 2, 3, and 4 of the second transmitter equalization register of the first communication lane interface of the second communication device.

Example 104 includes one or more machine readable storage media comprising a plurality of instructions stored thereon that, in response to execution, cause a first communication device to load requested transmitter equalization settings into a transmitter equalization register of a first communication lane interface of the first communication device, wherein the first communication lane interface of the first communication device is communicatively coupled with a first communication lane interface of a second communication device via a chip-to-chip communication link, and set a request flag of a transmitter equalization register of the first communication lane interface of the first communication device.

Example 105 includes the subject matter of Example 104, and wherein to set the request flag comprises to set bit 15 of the transmitter equalization register.

Example 106 includes the subject matter of any of Examples 104 and 105, and wherein to load the requested transmitter equalization settings comprises to set a pre-cursor requested register bank of the transmitter equalization register to a first desired value and set a post-cursor requested register bank of the transmitter equalization register to a second desired value.

Example 107 includes the subject matter of any of Examples 104-106, and wherein to set the pre-cursor requested register bank comprises to set bits 10 and 11 of the transmitter equalization register, and to set the post-cursor requested register bank comprises to set bits 12, 13, and 14 of the transmitter equalization register.

Example 108 includes the subject matter of any of Examples 104-107, and wherein the transmitter equalization register comprises a pre-cursor local register bank, a post-cursor local register bank, a pre-cursor remote register bank, a post-cursor remote register bank, a pre-cursor request register bank, a post-cursor request register bank, and the request flag.

Example 109 includes the subject matter of any of Examples 104-108, and wherein the pre-cursor local register bank comprises bits 0 and 1 of the transmitter equalization register; the post-cursor local register bank comprises bits 2, 3, and 4 of the transmitter equalization register; the pre-cursor remote register bank comprises bits 5 and 6 of the transmitter equalization register; the post-cursor remote register bank comprises bits 7, 8, and 9 of the transmitter equalization register; the pre-cursor request register bank comprises bits 10 and 11 of the transmitter equalization register; the post-cursor request register bank comprises bits 12, 13, and 14 of the transmitter equalization register; and the request flag comprises bit 15 of the transmitter equalization register.

The invention claimed is:

1. A station management entity of a communication controller of a communication system for performing transmitter equalization, the station management entity comprising:
 a transmitter equalization module to:
  read, via a dedicated communication bus established between the station management entity and a plurality of communication devices of the communication system, local transmitter equalization settings from a first transmitter equalization register of a first communication lane interface of a first communication device; and
  write, via the dedicated communication bus, the local transmitter equalization settings of the first communication lane interface of the first communication device to a first transmitter equalization register of a first communication lane interface of a second communication device,
  wherein the first communication lane interface of the first communication device is communicatively coupled with the first communication lane interface of the second communication device via a chip-to-chip communication link different from the dedicated communication bus,
  wherein the local transmitter equalization settings are to be used by the first communication device to filter a signal to be sent from the first communication device to the second communication device.

2. The station management entity of claim 1, wherein the dedicated communication bus comprises a management data input/output (MDIO) bus.

3. The station management entity of claim 1, wherein:
 to read the local transmitter equalization settings comprises to (i) read a pre-cursor local value from a pre-cursor local setting register bank of the first transmitter equalization register of the first communication lane interface of the first communication device and (ii) read a post-cursor local value from a post-cursor local setting register bank of the first transmitter equalization register of the first communication lane interface of the first communication device, and
 to write the local transmitter equalization settings comprises to (i) write the pre-cursor local value to a pre-cursor remote setting register bank of the first transmitter equalization register of the first communication lane interface of the second communication device and (ii) write the post-cursor local value to a post-cursor remote setting register bank of the first transmitter equalization register of the first communication lane interface of the second communication device.

4. The station management entity of claim 1, wherein the transmitter equalization module is further to read, via the dedicated communication bus, a request flag from the first transmitter equalization register of the first communication lane interface of the second communication device.

5. The station management entity of claim 4, wherein the transmitter equalization module is further to:
 read, via the dedicated communication bus, requested transmitter equalization settings from the first transmitter equalization register of the first communication lane interface of the second communication device; and
 write, via the dedicated communication bus, the requested transmitter equalization settings of the first communication lane interface of the second communication device to the first transmitter equalization register of the first communication lane interface of the first communication device in response to the request flag being true.

6. The station management entity of claim 5, wherein:
 to read the requested transmitter equalization settings comprises to (i) read a pre-cursor requested value from a pre-cursor request setting register bank of the first transmitter equalization register of the first communication lane interface of the second communication device and (ii) read a post-cursor requested value from a post-cursor request setting register bank of the first transmitter equalization register of the first communication lane interface of the second communication device and
 to write the requested transmitter equalization settings comprises to (i) write the pre-cursor requested value to a pre-cursor local setting register bank of the first transmitter equalization register of the first communication lane interface of the first communication device and (ii) write the post-cursor requested value to a post-cursor local setting register bank of the first transmitter equalization register of the first communication lane interface of the first communication device.

7. The station management entity of claim 5, wherein the transmitter equalization module is further to, after the requested transmitter equalization settings of the first communication lane interface of the second communication device have been written to the first transmitter equalization register of the first communication lane interface of the first communication device:
  re-read, via the dedicated communication bus, the local transmitter equalization settings from the first transmitter equalization register of the first communication lane interface of the first communication device; and
  re-write, via the dedicated communication bus, the local transmitter equalization settings of the first communication lane interface of the first communication device to the first transmitter equalization register of the first communication lane interface of the second communication device.

8. The station management entity of claim 4, wherein the transmitter equalization module is, in response to the request flag being false, further to:
  read, via the dedicated communication bus, local transmitter equalization settings from a second transmitter equalization register of the first communication lane interface of the second communication device; and
  write, via the dedicated communication bus, the local transmitter equalization settings of the first communication lane interface of the second communication device to a second transmitter equalization register of the first communication lane interface of the first communication device,
  wherein the second transmitter equalization register of the first communication lane interface of the second communication device is of a communication direction different from the first transmitter equalization register of the first communication lane interface of the second communication device, and
  wherein the second transmitter equalization register of the first communication lane interface of the first communication device is of a communication direction different from the first transmitter equalization register of the first communication lane interface of the first communication device.

9. The station management entity of claim 8, wherein:
  to read the local transmitter equalization settings from the second transmitter equalization register of the first communication lane interface of the second communication device comprises to (i) read a pre-cursor local value from a pre-cursor local setting register bank of the second transmitter equalization register of the first communication lane interface of the second communication device and (ii) read a post-cursor local value from a post-cursor local setting register bank of the second transmitter equalization register of the first communication lane interface of the second communication device, and
  to write the local transmitter equalization settings to the second transmitter equalization register of the first communication lane interface of the first communication device comprises to (i) write the pre-cursor local value to a pre-cursor remote setting register bank of the second transmitter equalization register of the first communication lane interface of the first communication device and (ii) write the post-cursor local value to a post-cursor remote setting register bank of the second transmitter equalization register of the first communication lane interface of the first communication device.

10. The station management entity of claim 8, wherein the transmitter equalization module is further to read, via the dedicated communication bus, a request flag from the second transmitter equalization register of the first communication lane interface of the first communication device.

11. The station management entity of claim 10, wherein the transmitter equalization module is further to:
  read, via the dedicated communication bus, requested transmitter equalization settings from the second transmitter equalization register of the first communication lane interface of the first communication device; and
  write, via the dedicated communication bus, the requested transmitter equalization settings of the first communication lane interface of the first communication device to the second transmitter equalization register of the first communication lane interface of the second communication device in response to the request flag being true.

12. The station management entity of claim 11, wherein:
  to read the requested transmitter equalization settings comprises to (i) read a pre-cursor requested value from a pre-cursor request setting register bank of the second transmitter equalization register of the first communication lane interface of the first communication device and (ii) read a post-cursor requested value from a post-cursor request setting register bank of the second transmitter equalization register of the first communication lane interface of the first communication device, and
  to write the requested transmitter equalization settings comprises to (i) write the pre-cursor requested value to a pre-cursor local setting register bank of the second transmitter equalization register of the first communication lane interface of the second communication device and (ii) write the post-cursor requested value to a post-cursor local setting register bank of the second transmitter equalization register of the first communication lane interface of the second communication device.

13. The station management entity of claim 11, wherein the transmitter equalization module is further to, after the requested transmitter equalization settings of the first communication lane interface of the first communication device have been written to the second transmitter equalization register of the first communication lane interface of the second communication device:
  re-read, via the dedicated communication bus, the local transmitter equalization settings from the second transmitter equalization register of the first communication lane interface of the second communication device; and
  re-write, via the dedicated communication bus, the local transmitter equalization settings of the first communication lane interface of the first communication device to the second transmitter equalization register of the first communication lane interface of the first communication device.

14. A first communication device for communicating with a second communication device, the first communication device comprising:
  a chip-to-chip interface comprising a first communication lane interface to communicate with a first communication lane interface of a second communication device over a chip-to-chip communication link, the first communication lane interface comprising a transmitter, a receiver, and a transmitter equalization register; and
  a request module to request transmitter equalization of the first communication lane interface, wherein the request module is to set a request flag of the transmitter equalization register to request the transmitter equalization, wherein the request flag indicates to a station management entity that the station management entity is to perform transmitter equalization on the second communication device with use of settings of the transmitter equalization register, wherein the chip-to-chip interface is further to receive, from the second communication device, a signal that has been filtered based on the settings of the transmitter equalization register.

15. The first communication device of claim 14, wherein the transmitter equalization register comprises a pre-cursor local register bank, a post-cursor local register bank, a pre-cursor remote register bank, a post-cursor remote register bank, a pre-cursor request register bank, a post-cursor request register bank, and the request flag.

16. The first communication device of claim 14, wherein the request module is further to load requested transmitter equalization settings into the transmitter equalization register.

17. The first communication device of claim 16, wherein to load the requested transmitter equalization settings comprises to set a pre-cursor requested register bank of the transmitter equalization register to a first desired value and set a post-cursor requested register bank of the transmitter equalization register to a second desired value.

18. One or more non-transitory, machine readable storage media comprising a plurality of instructions stored thereon that, in response to execution, cause a station management entity to:
    read, and over a dedicated communication bus established between the station management entity and a plurality of communication devices of a communication system, local transmitter equalization settings from a first transmitter equalization register of a first communication lane interface of a first communication device; and
    write, over the dedicated communication bus, the local transmitter equalization settings of the first communication lane interface of the first communication device to a first transmitter equalization register of a first communication lane interface of a second communication device,
    wherein the first communication lane interface of the first communication device is communicatively coupled with the first communication lane interface of the second communication device via a chip-to-chip communication link different from the dedicated communication bus,
    wherein the local transmitter equalization settings are to be used by the first communication device to filter a signal to be sent from the first communication device to the second communication device.

19. The one or more non-transitory, machine readable storage media of claim 18, wherein to:
    read the local transmitter equalization settings comprises to read, over a management data input/output (MDIO) bus, the local transmitter equalization settings, and
    write the local transmitter equalization settings comprises to write, over the MDIO bus, the local transmitter equalization settings.

20. The one or more non-transitory, machine readable storage media of claim 18, wherein to:
    read the local transmitter equalization settings comprises (i) to read a pre-cursor local value from a pre-cursor local setting register bank of the first transmitter equalization register of the first communication lane interface of the first communication device and (ii) to read a post-cursor local value from a post-cursor local setting register bank of the first transmitter equalization register of the first communication lane interface of the first communication device, and
    write the local transmitter equalization settings comprises (i) to write the pre-cursor local value to a pre-cursor remote setting register bank of the first transmitter equalization register of the first communication lane interface of the second communication device; and (ii) to write the post-cursor local value to a post-cursor remote setting register bank of the first transmitter equalization register of the first communication lane interface of the second communication device.

21. The one or more non-transitory, machine readable storage media of claim 18, wherein the plurality of instructions further cause the station management entity to read, over the dedicated communication bus, a request flag from the first transmitter equalization register of the first communication lane interface of the second communication device.

22. The one or more non-transitory, machine readable storage media of claim 21, wherein the plurality of instructions further cause the station management entity to:
    read, over the dedicated communication bus, requested transmitter equalization settings from the first transmitter equalization register of the first communication lane interface of the second communication device; and
    write, over the dedicated communication bus, the requested transmitter equalization settings of the first communication lane interface of the second communication device to the first transmitter equalization register of the first communication lane interface of the first communication device in response to the request flag being true.

23. The one or more non-transitory, machine readable storage media of claim 22, wherein the plurality of instructions further cause the station management entity to, subsequently to the writing of the requested transmitter equalization settings of the first communication lane interface of the second communication device to the first transmitter equalization register of the first communication lane interface of the first communication device,
    re-read, over the dedicated communication bus, the local transmitter equalization settings from the first transmitter equalization register of the first communication lane interface of the first communication device; and
    re-write, over the dedicated communication bus, the local transmitter equalization settings of the first communication lane interface of the first communication device to the first transmitter equalization register of the first communication lane interface of the second communication device.

24. The one or more non-transitory, machine readable storage media of claim 21, wherein the plurality of instructions further cause the station management entity to, in response to the request flag being false,
    read, over the dedicated communication bus, local transmitter equalization settings from a second transmitter equalization register of the first communication lane interface of the second communication device; and
    write, over the dedicated communication bus, the local transmitter equalization settings of the first communication lane interface of the second communication device to a second transmitter equalization register of the first communication lane interface of the first communication device,
    wherein the second transmitter equalization register of the first communication lane interface of the second communication device is of a communication direction different from the first transmitter equalization register of the first communication lane interface of the second communication device, and wherein the second transmitter equalization register of the first communication lane interface of the first communication device is of a communication direction different from the first transmitter equalization register of the first communication lane interface of the first communication device.

25. The one or more non-transitory, machine readable storage media of claim 24, wherein the plurality of instructions further cause the station management entity to read, over the dedicated communication bus, a request flag from the second transmitter equalization register of the first communication lane interface of the first communication device.

26. The one or more non-transitory, machine readable storage media of claim 25, wherein the plurality of instructions further cause the station management entity to:
   read, over the dedicated communication bus, requested transmitter equalization settings from the second transmitter equalization register of the first communication lane interface of the first communication device; and
   write, over the dedicated communication bus, the requested transmitter equalization settings of the first communication lane interface of the first communication device to the second transmitter equalization register of the first communication lane interface of the second communication device in response to the request flag being true.

27. The one or more non-transitory, machine readable storage media of claim 26, wherein the plurality of instructions further cause the station management entity to, subsequently to the writing of the requested transmitter equalization settings of the first communication lane interface of the first communication device to the second transmitter equalization register of the first communication lane interface of the second communication device,
   re-read, over the dedicated communication bus, the local transmitter equalization settings from the second transmitter equalization register of the first communication lane interface of the second communication device; and
   re-write, over the dedicated communication bus, the local transmitter equalization settings of the first communication lane interface of the first communication device to the second transmitter equalization register of the first communication lane interface of the first communication device.

28. One or more non-transitory, machine readable storage media comprising a plurality of instructions stored thereon that, in response to execution, cause a first communication device to:
   load requested transmitter equalization settings into a transmitter equalization register of a first communication lane interface of the first communication device, wherein the first communication lane interface of the first communication device is communicatively coupled with a first communication lane interface of a second communication device via a chip-to-chip communication link,
   set a request flag of a transmitter equalization register of the first communication lane interface of the first communication device, wherein the request flag indicates to a station management entity that the station management entity is to perform transmitter equalization on the second communication device with use of the requested transmitter equalization settings, and
   to receive, from the second communication device, a signal that has been filtered based on the requested transmitter equalization settings.

29. The one or more non-transitory, machine readable storage media of claim 28, wherein to load the requested transmitter equalization settings comprises to set a pre-cursor requested register bank of the transmitter equalization register to a first desired value and setting a post-cursor requested register bank of the transmitter equalization register to a second desired value.

30. The one or more non-transitory, machine readable storage media of claim 28, wherein the transmitter equalization register comprises a pre-cursor local register bank, a post-cursor local register bank, a pre-cursor remote register bank, a post-cursor remote register bank, a pre-cursor request register bank, a post-cursor request register bank, and the request flag.

* * * * *